United States Patent
Farrell

(10) Patent No.: US 9,622,025 B2
(45) Date of Patent: Apr. 11, 2017

(54) ASSET TAGS

(71) Applicant: Enovate Medical, LLC, Murfreesboro, TN (US)

(72) Inventor: Arlow Farrell, Murfreesboro, TN (US)

(73) Assignee: Enovate Medical, LLC, Murfreesboro, TN (US)

( * ) Notice: Subject to any disclaimer, the term of this patent is extended or adjusted under 35 U.S.C. 154(b) by 0 days.

(21) Appl. No.: 15/271,158

(22) Filed: Sep. 20, 2016

(65) Prior Publication Data

US 2017/0013398 A1    Jan. 12, 2017

Related U.S. Application Data

(63) Continuation of application No. 14/961,490, filed on Dec. 7, 2015, now abandoned.

(60) Provisional application No. 62/146,084, filed on Apr. 10, 2015.

(51) Int. Cl.
*H04B 7/00* (2006.01)
*H04W 4/00* (2009.01)
*G01S 1/68* (2006.01)

(52) U.S. Cl.
CPC .............. *H04W 4/008* (2013.01); *G01S 1/68* (2013.01)

(58) Field of Classification Search
CPC ......... H04W 4/008; G01S 5/08; G01S 5/0226
USPC ...................................................... 455/41.2
See application file for complete search history.

(56) References Cited

U.S. PATENT DOCUMENTS

| | | | |
|---|---|---|---|
| 2014/0329536 A1* | 11/2014 | Tian | H04W 64/00 455/456.1 |
| 2014/0368334 A1* | 12/2014 | Tian | G01S 5/0289 340/539.13 |
| 2015/0168543 A1* | 6/2015 | Tian | G01S 11/02 342/458 |
| 2015/0169911 A1* | 6/2015 | Tian | G06K 7/10366 340/8.1 |
| 2015/0178846 A1* | 6/2015 | Feinschreiber | G06Q 40/06 705/36 R |

* cited by examiner

*Primary Examiner* — April G Gonzales
(74) *Attorney, Agent, or Firm* — Nathan J. Bailey; Waller Lansden Dortch & Davis, LLP

(57) ABSTRACT

A method and apparatus for scanning, by an asset tag manager during a scanning window, for wireless broadcasts from beacon devices. The method further filters the wireless broadcasts to generate a subset of the wireless broadcasts. The method continues by identifying, within the subset of the wireless broadcasts, a first wireless broadcast with a first data packet in view of an indication that a first beacon device is within a specified distance from the asset tag manager. The method proceeds by parsing the first data packet to locate a first beacon identifier associated with a first beacon device. The method also creates a second data packet with the first beacon identifier and an asset tag identifier associated with the asset. The method transmits a second wireless broadcast comprising the second data packet, the second wireless broadcast to be received by a hub.

20 Claims, 10 Drawing Sheets

ASSET TAGS

RELATED APPLICATIONS

This application claims the benefit of U.S. Provisional Application No. 62/146,084 filed on Apr. 10, 2015, the contents of which are hereby incorporated by reference herein.

BACKGROUND

Asset management systems may be systems used to manage an entire or part of a lifecycle of an asset. An entity may identify assets as objects of value to the entity. Assets may be tangible objects, such as buildings, hardware, devices, etc., or may be intangible objects such as software, information, intellectual property, etc. Asset management systems may help an entity design, deploy, operate, maintain, track, upgrade, and/or dispose of assets. As part of asset management, an entity may use an asset tracking system to identify, track the movement, and/or manage the entity's assets.

BRIEF DESCRIPTION OF THE DRAWINGS

The present disclosure is illustrated by way of example, and not by limitation, in the figure of the accompanying drawings.

DETAILED DESCRIPTION

Figure 1A:
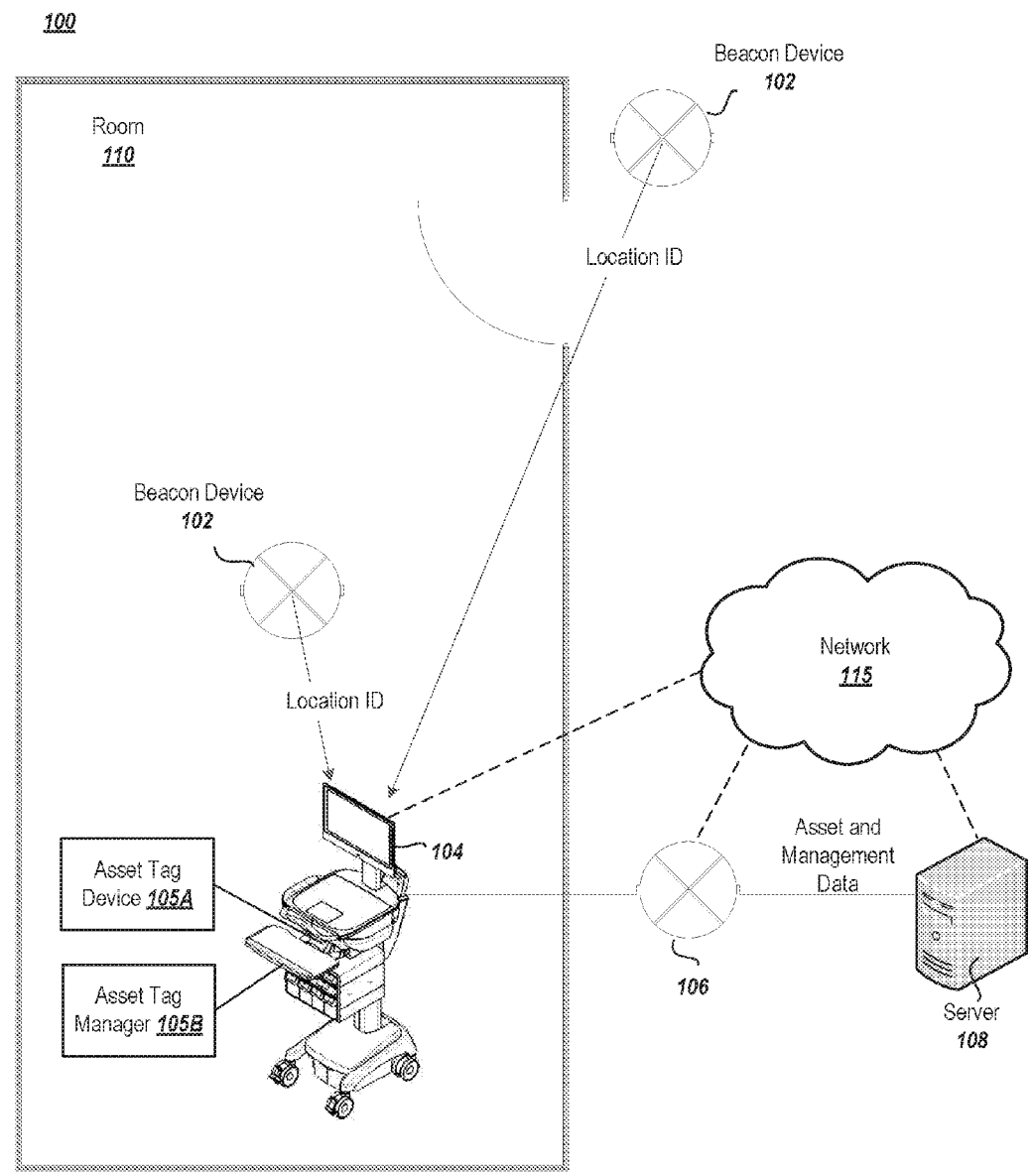
FIG. 1A illustrates a communication flow of asset and management information in a medical management system (MMS) according to various embodiments.

The assets of an entity, such as a large-scale enterprise, may provide tracking and management challenges. For example, the assets of a large-scale enterprise may be numerous and/or spread over multiple locations. Manual paperwork systems for tracking and managing assets may be resource intensive, time-intensive, and prone to errors. For example, when an employee checks out equipment, the employee can write down the time the asset was checked out and the time that the asset was checked back in. In this example, an employee may forget to write down when they checked an asset in or out, fail to return an asset, lie about equipment usage, and so forth.

Electronic asset tracking systems (ATS) using barcode labels or radio frequency identification (RFID) may be used to decrease the time-intensiveness and errors associated with manual paperwork systems. However, a barcode label or an RFID tag may still demand a user to manually scan an asset to track information, may not provide additional useful information, and the implementation of such systems may be costly and not suitable for many environments. For example, an ATS can use barcode labels or radio frequency identification (RFID) tags to track assets. The barcode labels or RFID tags can be attached to each asset and when the asset is checked in or out, the user can scan the barcode label or RFID tag using a scanner. However, a barcode label or an RFID tag may still demand a user to manually scan an asset to track information. For example, a barcode label or RFID tag typically require either movement of assets past scanners (e.g., palettes leaving a warehouse or airline passengers moving past a magnetic detector) or employees walking around a facility to verify manually that the data matches the records (e.g., stock takes). Collection of asset information using a traditional ATS can be difficult. For example, equipment that is on a floor, under desks, behind monitors, and so forth, can have a barcode label or an RFID tags in inconvenient or hard to find locations. Additionally, these techniques can physically locate the asset and can require personnel to physically collect the asset information. Use of manual scanners can be slow and impractical for many environments.

Assets of all kinds may be tracked. An asset may refer to an object of value to the entity. Assets may be tangible objects, such as buildings, hardware, devices, etc., or may be intangible objects such as software, information, intellectual property, etc. As used herein, a hard asset is an inanimate tangible object to be tracked, whereas a soft asset refers to both intangible objects to be tracked, as well as humans to which the asset tag device is attached or otherwise secured. The assets can be used to track medial assets, medical personnel, medical equipment, patients, or the like. The assets can also be non-medical assets. For example, the asset management system can be used to track assets in a corporate environment or a military environment. For example, the individuals may be an employee of any organization, military personnel in a military enterprise setting, government workers at any level in government, and medical personnel in a medical facility setting, or the like. When the term "asset" is referred to herein, it may be with relation to an asset accessible by any of these types of employees or personnel that may have access to confidential or sensitive information through different kinds of assets, such as mobile devices, computers, work stations and the like. For clarity and simplified explanation, the present disclosure is primarily described with reference to medical assets in a medical setting, but is not so limited.

A medical asset may include equipment such as a medical cart, ventilators, an IV pole, a tablet computer, a battery pack, all in one (AIO) personal computer, and so forth. A military asset may include a mobile or stationary computer, a radio system, a workstation and a weapons system and the like. A government asset may include a mobile or stationary computer, a workstation, an authentication pad and the like. Because some assets involve computing devices (such as a medical cart, a tablet or personal computer), these assets may provide access to confidential or sensitive patient information records in a medical setting, a military setting, a government setting and in a business setting. Tracking assets within these environments can be a challenge when the assets may be distributed throughout a medical facility such as a hospital, nursing home or medical clinic (or a military or government facility) and are generally difficult to keep under constant observation at all times.

The following describes embodiments of an asset management system in the context of a medical management system (MMS) that is used to track medical assets.

FIG. 1A illustrates a communication flow of asset and management information in a medical management system (MMS) 100 according to various embodiments, in addition to aspects of a real-time location system (RTLS) that works with the MMS 100. The communication flow may originate in a location such as a room 110, and may include beacon devices 102 and data sent from an asset 104 (e.g., a medical cart is shown). The asset 104 may be coupled with an asset tag device 105A or may include an asset tag manager 105B that runs on the asset 104 to determine a location of the asset 104. An asset tag device 105A may be an electronic device coupled to an asset or integrated into the asset and used as part of an asset-tracking system (ATS), such as a real-time locating system (RTLS). An asset tag device may be a small (e.g., size of a U.S. quarter), resource-constrained (i.e., low processing power, limited memory, and/or limited battery life) device used to transmit data, such as a beacon identifier, to a more powerful central device. The central device, such as a server computer system (also referred to as server), may make a determination of location of an asset tag device and/or asset in view of the transmitted data. An asset tag device may be a wireless device and transmit data using a wireless communication protocol. An asset tag device may be a low-power device and/or be battery powered. An asset tag device may use a rechargeable battery, such as a lithium-ion rechargeable battery. An asset tag device may be coupled to or integrated into an asset in a variety of ways. For example, an asset tag device may be a discrete hardware device that is physically fixed to a hard asset. An asset tag device may be a hardware device that is integrated into the hardware of an asset. A third party device, such as a mobile phone, may be converted into an asset tag device by loading the asset tag software (e.g., asset tag manager) and leveraging the hardware of the third party device to perform the functions of the asset tag device.

The data (including the location) may flow through a communication hub 106 (or other network device) and arrive at a server 108 (such as a medical database and/or an authentication server). In some embodiments, the data also, or alternatively, flows through a communications network 115, where the communications network 115 may include the communication hub 106. The data flow may also flow in the reverse direction from the server 108 and/or the communication hub 106 to the asset 104, e.g., in response to a request for medical information or records on a patient. The data may include asset and/or management data, medical information, patient information, authentication data, and other personal and security-related information and the like.

The MMS 100 may include multiple assets 104. The beacon devices 102 may be associated with fixed locations and may provide a location identifier (ID) for asset tag device 105A (or 105B) to detect, such that the asset tag device 105A (or 105B) may determine a current location, which the assets may transmit through the communication hub 106 to the server 108. The beacon device 102 may identify or be associated with any type of location, including a room, a hallway, a common or conference room, and/or a grid location.

The beacon device 102 may include a circuit board within a housing, the circuit board containing a processor (or discrete logic or controller or microcontroller), memory (non-volatile and/or volatile memory), a battery (or other power source), and a transceiver primarily for transmitting. The beacon device 102 may be programmed to transmit a beacon signal containing data to identify the beacon device to other devices, such as to the asset tag device 105A or to the asset tag manager 105B running on a host machine of the asset 104.

In one example, the beacon device 102 may communicate with the asset tag device 105A and/or the asset tag manager 105B through a personal area network (PAN), such as, e.g., with Bluetooth® technology developed by the Bluetooth Special Interest Group (SIG). In another example, the PAN may be created with Bluetooth® low energy (BLE) technology (also developed by Bluetooth SIG) that may be used to track the assets 104. For example, a BLE-based beacon may be associated with an asset in the MMS 100 to communicate asset and/or management information of the asset.

In another example, the beacon device 102 may be an active or passive radio frequency identification (RFID) tag that transmits a unique RFID number. The RFID number or identifier may be correlated at the server 108 with a certain location such as may have been pre-programmed at the server 108 or within a distributed MMS 100. In this example, the asset tag device 105A and/or the asset tag manager 105B may be or include an interrogator that interrogates the RFID tag of the beacon device 102 to determine the RFID number or identifier of the beacon device 102. When the beacon device 102 is an active RFID tag, the asset tag device 105A and/or the asset tag manger 105B may receive the actively transmitted RFID number of identifier as transmitted by the beacon device 102.

Figure 2:
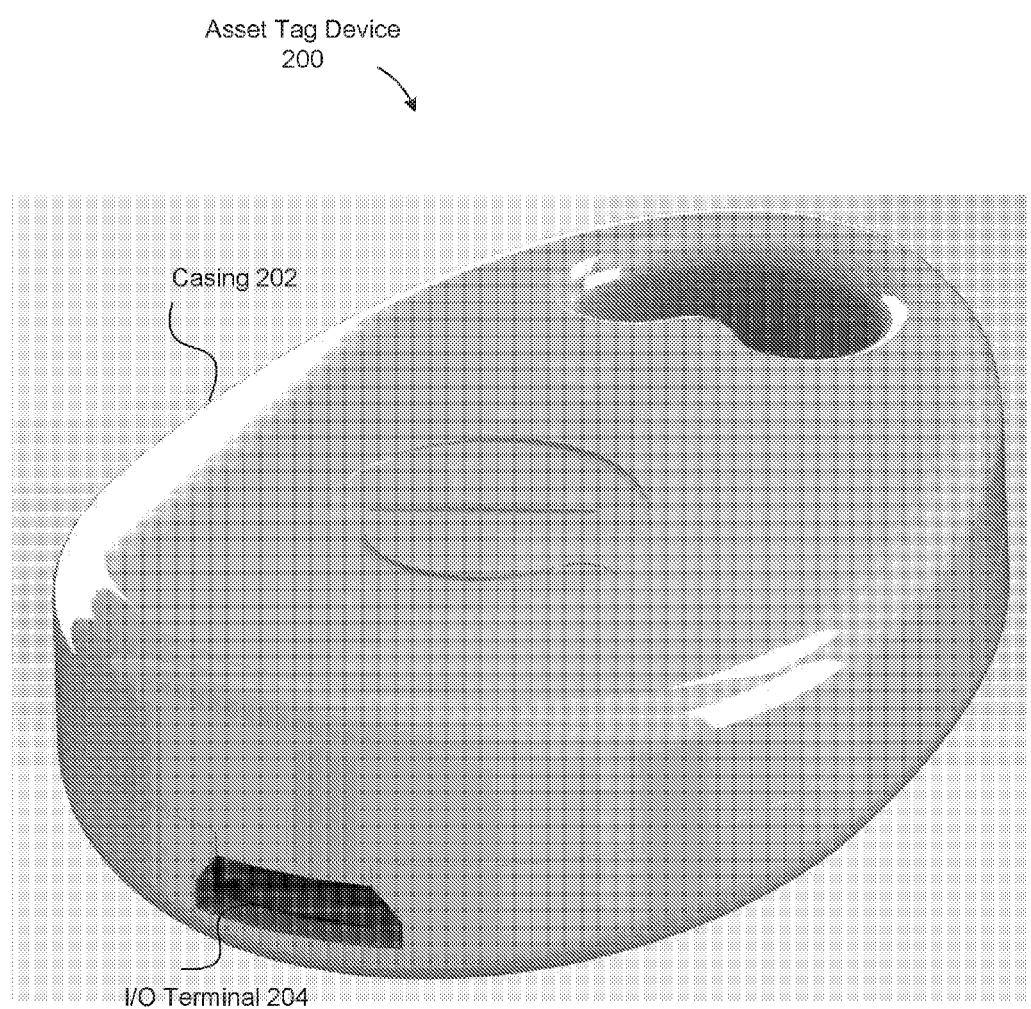
FIG. 2 illustrates an asset tag device, according to another embodiment.

The asset tag device 105A (e.g., a non-integrated asset tag device) may be implemented in hardware and include a circuit board within a housing as depicted in FIG. 2, the circuit board containing a processor, memory (non-volatile and/or volatile memory), a battery, and a transceiver. The transceiver may be a third-party integrated circuit, such as an RF module, e.g., a Bluetooth® chip, an RFID interrogator and/or receiver or the like. The asset tag device may be performed by processing logic comprising hardware, software, firmware or any combination thereof.

The asset tag manager 105B (e.g., an integrated asset tag device) may be a software program (including instructions) that may utilize a processor, memory, transceiver and the like of a host machine of the asset 104, such as the medical cart (all-in-one (AOI)), any medical device in which the asset tag is integrated, or any device when used in non-medical applications.

The asset tag device 105A and/or the assets 104 may be tracked with a real-time location system (RTLS) that determines the location of whatever is tagged (or otherwise tracked by identifying a location of beacon devices 102 in proximity of the assets 104). The tracked entities may include an asset or equipment, a MSM and/or patient(s), for example. The communications hub 106 may be wired or wireless and may direct data between the assets and to (and from) the assets 104 and the server 108.

In one example, the beacon device may broadcast a location ID to any device located within the room 110. In this example, when the asset 104 receives the location ID from the beacon device 102, the asset 104 may determine its location. In another example, the asset 104 may measure a received signal strength indication (RSSI) from the beacon device 102 to determine a location of the device within a radius or area for which the beacon device is designated.

For example, the asset 104 may use the received location ID from the beacon device 102 to determine that the asset 104 is located in an identified room. The asset 104 may also use the RSSI to determine a location of the asset 104 within the room, such as within a threshold of location accuracy (e.g., within X distance from the beacon device 102). In one example, a room may include multiple beacon devices 102. The asset 104 may receive multiple location IDs from the multiple beacon devices 102 and use the RSSI of the different location IDs to determine the location of the asset 104 within the room. For example, the asset 104 may use the RSSI of the different location IDs to triangulate the location of the asset 104 in the room. In another example, the beacon device 102 may be located at different locations. For example, the beacon device 102 may be located in a hallway, in a lobby, in a stairwell, in a room, in a parking lot, and so forth. When the asset tag device 105A (or asset tag manager 105B) determines its location, the asset tag device 105A (or asset tag manager 105B) may communicate asset information (such as location information, asset management information, and so forth) to a closest communication hub 106.

In another example, the asset tag device 105A and/or the asset tag manager 105B can append the location ID to the asset information and communicate the appended asset information to the communication hub 106. The communication hub 106 can analyze the appended information to determine the location of the asset 104 using the location ID and the asset information. For example, the communication hub 106 can access a database that defines the locations of different beacon devices with different location IDs. The communication hub 106 can compare the received location ID from the asset tag device 105A and/or the asset tag manager 105B with the location IDs in the database to find a matching pair of location IDs and associate the defined location of the location ID with the asset 104.

In one example, the communication hub 106 may be a device (such as a communication plate) mounted to a wall. In another example, the communication hub 106 may be integrated into a construction of a location. For example, the communication hub 106 may be integrated into a floor, ceiling, or wall of a facility, for example. In another example, the communication hub 106 may be software on the server 108.

In one example, the communication hub 106 may be located at a different location than the room 110 (such as a central location on the floor where the device is located or a central location in the building where the device is located). When the communication hub 106 receives the asset information from the asset 104, the communication hub 106 may relay the information to a server 108. In one example, the communication hub 106 may receive information from different devices. When the communication hub 106 receives the information from the different devices, the communication hub 106 may aggregate the data and send the aggregated asset information to the server 108.

One advantage of the asset tag device 105A (or asset tag manager 105B) determining its location and sending the asset management information to the communication hub 106 may be to enable the beacon device 102 to be small and low energy. For example, because the beacon device 102 broadcasts the location ID, the beacon device 102 may consume a small amount of power (such as a 1-2 mAh per day) and may be powered by a small battery for an extended period of time. The asset tag device 105A may have a separate power supply that may be recharged more easily than the beacon device 102. Another advantage of the asset tag device 105A (or asset tag manager 105B) communicating the asset information may be that the asset the asset tag device 105A may select the information of the asset tag device 105A to be communicated to the communication hub 106 and communicate the information in real-time and directly to the communication hub 106 to reduce communication interference from multiple devices.

In one example, the MMS 100 may track the assets 104 in real-time or substantially real-time. For example, the asset 104 may continuously communicate asset and management information to the communication hub 106.

In another example, the MMS 100 may track the assets on a periodic basis. For example, the asset 104 may communicate asset and management information to the communication hub 106 on a periodic basis. In another example, the communication hub 106 may transmit a request to the asset 104 to communicate the asset and management information. When the asset 104 receives the request, the asset 104 may communicate the asset and management information to the communication hub 106.

In one example, the MMS may include an implementation system to map a facility where assets may be managed, e.g., determine a schematic or layout of the facility. In another example, the implementation system may include software to determine a schematic or layout of the facility, including rooms, stairway objects, hallway objects, and so forth, based on a digital plan and/or a computer-assisted built plan within the software. In another example, a user may use a scanner, such as a three-dimensional (3D) scanner and walk around the facility collecting layout information, where the software may use the information from the scanner to determine the layout of the facility.

With further reference to FIG. 1, when the implementation software has determined a layout of the facility, the software may associate the beacon device 102 and/or the communication hub 106 may be associated with the layout of the facility. For example, the beacon devices 102 and/or the communication hubs 106 in a facility may have a unique ID. When the facility layout is determined, the implementation software may receive input from an input device (such as a mouse, a keyboard, a stylus, a touch screen, and so forth) associating the different unique IDs with locations on the facility layout.

In another example, locations in the facility layout may have unique IDs associated with the location. In this example, an assistance device (such as a scanner or a communication device) may be taken to one or more locations in the facility, where the location ID may be selected, the assistance device may scan or communicate with the beacon device 102 and/or the communication hub 106, and the beacon device 102 and/or the communication hub 106 may be associated with the location ID. In another example, when a device is located at a facility location, the assistance device may scan the location for the beacon devices 102 and/or the communication hubs 106 (such as by using by using Bluetooth® scanning) and associate the beacon device 102 and/or the communication hub 106 scanner in the location with a location ID. For example, a user may walk into a room with a first location ID, use a tablet with Bluetooth® technology to scan the room for the beacon devices 102 and/or the communication hubs 106, and the software may associate the beacon devices 102 and/or the communication hubs 106 detected by the tablet with the first location ID. The user may repeat this process for multiple locations in the facility.

In yet another example, the beacon devices 102 may have a predefined number or identifier (ID). When a layout of the building is compiled, the user may use a graphical user interface (GUI) to select which beacon device is located in each room, hallway, conference room and the like.

An advantage of the implementation of the MMS 100 may be to enable integration of the MMS into a preexisting facility, e.g., the MMS may be installed in a preexisting facility and the implementation system may map the preexisting facility. Another advantage of the MMS may be that the installation and implementation of the MMS may enable quick and efficient installation as the MMS may be installed and configured for a facility without invasively installing an asset management system. Another advantage of the MMS may be that the system may avoid interference by other devices by using the implementation system to determine optimal locations of the beacon devices 102 and/or the communication hubs 106.

Figure 1B:
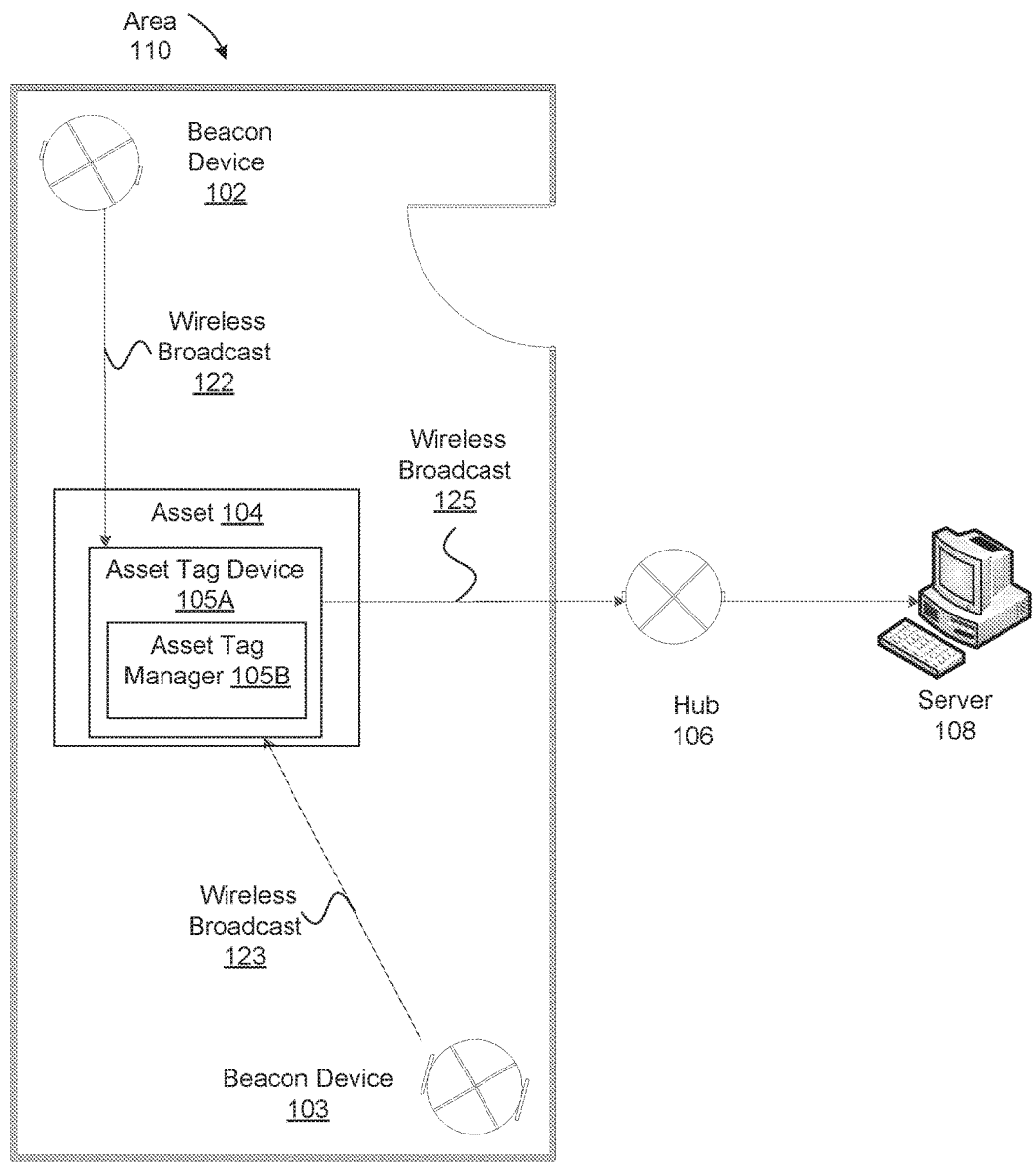
FIG. 1B illustrates an asset management system, according to one embodiment.

The asset management system can be used in other contexts, as described with respect to FIG. 1B. The details regarding the asset tag manager and asset tag device are described in more detail below with respect to FIG. 1B.

By way of introduction, the embodiments described herein use an asset tag device, which is coupled to an asset, that scans for wireless broadcasts from beacon devices located at fixed locations. It should be noted that beacon devices may not be at fixed locations, but their absolute or relative locations should be known to a communication hub. In other cases, the asset tag devices may communication with one another to determine locations without the use of beacon devices. The asset tag device filters and parses the wireless broadcasts to locate a beacon identifier, and transmits an updated wireless broadcast, including the beacon identifier and asset tag identifier, to a hub. It should be note that the asset tag device may not transmit the updated wireless broadcast if the asset tag device stays in the same location and the information is not updated. Although various embodiments herein describe the functionality of an asset tag device, the functionality may also be achieved by the asset tag manager in connection with a host device as described herein.

It should be also noted that examples provided herein of asset tag devices being used in hospital settings are provided for purposes of illustration, rather than limitation. It should be appreciated that asset tag devices, as well as other cooperating devices, may be used in different settings such as disaster relief operations, retail stores, and/or product warehouses.

FIG. 1B illustrates an asset management system, according to one embodiment. FIG. 1B further illustrates area 110. Area 110 includes beacon device 102 and beacon device 103 fixed to opposite corners of area 110. Beacon devices 102 and 103 may transmit wireless broadcast 122 and 123, respectively, using a wireless communication protocol compatible with asset tag device 105A. Asset 104 may be any asset as described herein. The asset tag device 105A may be physically coupled to asset 104. The asset tag device 105 may be attached to, disposed within, disposed on, or otherwise affixed to the asset 104, For example, the asset tag device 105A may be integrated into the hospital cart or other medical device, military equipment, business resource, or the like.

An asset tag device 105A may be an electronic device coupled to an asset 104 or integrated into the asset 104 and used as part of an asset-tracking system (ATS), such as a real-time locating system (RTLS). An asset tag device 105A may be a small (e.g., size of a U.S. quarter), resource-constrained (i.e., low processing power, limited memory, and/or limited battery life) device used to transmit data, such as a beacon identifier, to a more powerful central device, such as server 108. The server computer system (also referred to as server 108), may make a determination of location of an asset tag device 105A and/or asset 104 in view of the transmitted data. An asset tag device 105A may be a wireless device and transmit data using a wireless communication protocol. An asset tag device 105A may be a low-power device and/or be battery powered. An asset tag device 105A may use a rechargeable battery, such as a lithium-ion rechargeable battery. An asset tag device 105A may be coupled to or integrated into an asset 104 in a variety of ways. For example, an asset tag device 105A may be a discrete hardware device that is physically fixed to a hard asset. An asset tag device 105A may be a hardware device that is integrated into the hardware of an asset. A third party device, such as a mobile phone, may be converted into an asset tag device 105A by loading the asset tag software (e.g., asset tag manager 105B) and leveraging the hardware of the third party device to perform the functions of the asset tag. Asset tag may refer to asset tag device 105A and/or asset tag manager 105B. The asset tag device 105A includes an asset tag manager 105B, that is, the processing device of the asset tag device 105A executes instructions corresponding to the asset tag manger 105B to perform the functionality describe herein. In other embodiments, the asset tag manager 105B executes on a processing device of a host device, such as the AIO, or other medical asset. In some embodiments, asset tag manager 105B may be a software implementation of asset tag device 105A used to perform one or more functions of the asset tag device 105A. Asset tag manager 105B may be executed by a processing device (not shown).

It should be noted that an area, such as area 110, may refer a physical space delineated by the signal coverage of one or more beacon devices 102 and 103. It should be appreciated that an area 110 may be defined by software and correspond to the beacon device's physical location and associated wireless broadcast. For example, a large room may have multiple areas. Two beacon devices 102 and 103 located at one side of a room may delineate an area, while two other beacon devices at the other side of a room may delineate another area. Software may correlate the location of the beacon devices 102 and 103 and signal coverage of the beacon devices 102 and 103 to define an area, such as area 110. Using two or more beacon devices, such as beacon devices 102 and 103, to delineate an area may allow an asset management system to improve the accuracy of location determinations of assets. It also should be appreciated that while two beacon devices (i.e., beacon device 102 and 103) are illustrated in FIG. 1B as delineating area 110, the number of beacon devices is for purposes of illustration, rather than limitation. An area may be delineated by one or more beacon devices and may depend on a variety of factors such as available resources or system requirements.

A beacon device (also referred to as a location identification beacon) may be an electronic device fixed to a known location (and/or marking a fixed location) and used to transmit a data packet. The data packet may include a fixed parameter, such as a beacon identifier, which may be used to determine a relative location of an asset 104 or the asset tag device 105A (or 105B). For example, two different beacon devices 102 and 103 may be fixed to different corners of a room, each transmitting a wireless broadcast (i.e., broadcasts a signal). Each of the wireless broadcasts may contain a different beacon identifier representative of the different beacon devices. The wireless broadcasts may be received by an asset tag (105A and/or 105B). The asset tag (105A and/or 105B) may send the beacon identifiers and the asset tag identifier to a server 108. The server 108 may use the beacon identifiers to identify each beacon device 102 and 103, identify the known location of each beacon device 102 and 103, and determine the relative location of the asset tag (105A and/or 105B) to the beacon devices 102 and 103. In another embodiment, a beacon device 102 and 103 may be a small, resource-constrained (i.e., low processing power, limited memory, and/or limited battery life) device used to transmit data, such as a beacon identifier, to an asset tag (105A and/or 105B). A beacon device 102 and 103 may be wireless device transmitting data packets using a wireless communication protocol (e.g., BLE® or Wi-Fi®) compatible with an asset tag (105A and/or 105B). The beacon device 102 and 103 may be a low-power device and/or battery powered. The beacon identifier may be a unique value, such as a number, assigned to the beacon device by a developer and/or used to identify a beacon device. The beacon identifier could also be defined by an operator, such as an administrator of a hospital, a person setting up a military base, or the like. The beacon devices 102 and 103 can be installed in a location and then an operator can associate the location with the beacon device 102 and 103, for example. In one embodiment, the major identifier (2 bytes) and/or minor identifier (2 bytes) may be used as a beacon identifier. The major identifier and/or the minor identifier may be a serialized number. In one example the major identifier is unsigned integer used to group beacons with a same proximity ID. In another example, the minor identifier is an unsigned integer that differentiates beacons with the same proximity ID and major identifier.

The beacon identifier may be distinct from the universally unique identifier (UUID). A UUID is an identifier standard in software constructions, such as a 128-bit value, where each bit is defined by any of several variants. The UUID may uniquely identify (at least practically) information without significant central coordination. An example of a beacon device may utilize iBeacon® technology, developed by Apple, Inc. of Cupertino Calif. The iBeacon® technology is a protocol used by compatible hardware transmitters that broadcast their identifier to nearby portable electronic devices. Alternatively, other types of beacon devices may be used.

A broadcast may refer to the transmission of a signal containing data in a data packet. A wireless broadcast may be a type of broadcast and may refer to the transmission of a signal containing data without an electrical conductor, for example the transmission of a signal through the air. A wireless broadcast may include at least two types of broadcasts, an advertisement broadcast (also referred to as an advertisement) and a response broadcast (also referred to as a scan response). Any device, such as beacon device 102, beacon device 103, and asset tag device 105A may transmit a broadcast. Any device, such as asset 104, asset tag device 105A, asset tag manager 105B, and/or server 108 may scan and receive a broadcast, such as an advertisement broadcast or a response broadcast. In an advertising mode, a device (e.g., beacon device 102 and/or 103, asset tag 105A or 105B) may transmit (e.g., advertise) an advertisement broadcast including an advertisement data packet at certain times (e.g., once, over intervals or periods, or continuously) without receiving a request from another device (e.g., asset tag 105A, hub 106, or server 108) to transmit the advertisement data packet. The advertisement data packet is a data packet transmitted without receiving a request, from another device, for the data packet. In another embodiment, the device may transmit the advertisement broadcast in real-time. In a response mode, a device (e.g., beacon device 102, beacon device 103, asset tag 105A or 105B) may transmit a response broadcast including a response data packet in response to receiving a request from another device to transmit the response data packet. A requesting device may request a response for any reason, such as for asset tracking. A response data packet is a data packet transmitted in response to a request, from another device, to transmit the response data packet. A request may be transmitted by any device and may be multicast or unicast between the two devices. For example, asset tag device 105A (as well as hub 106 or server 108) may broadcast a request for a response data packet from beacon devices 102 or 103. In another embodiment, hub 106 or server 108 may send a request to asset 104, asset tag device 105A, or asset tag device 105B for a response data packet. It should be noted that any device may send a request for a response data packet. A request may be sent once, over intervals or periods, or continuously.

A data packet may refer to a signal including a formatted unit of data. A data packet may include information in the form on one or more identifiers. For example, in the control information (i.e., data used by the network to deliver the data packet), sequencing information, a length of the payload, source and destination addresses, etc. may each be considered an identifier. In another example, the user data of the data packet may include one or more identifiers. The user data may include company identifiers, source device information identifiers, identifiers of other manufacturing specific data (e.g., manufacturer identifier), wireless broadcast identifier (e.g., advertisement indicator identifier), location identifier, beacon identifier (e.g., a major identifier (ID) and/or minor identifier (ID)), battery identifier, etc. Examples of identifiers are provided for purposes of illustration, rather than limitation. It should be appreciated that different identifiers may be available. It should be appreciated that some or all of the identifiers included in a data packet may be prescribed by the particular wireless communication protocol used to transmit the data packet.

In one embodiment, an asset tag (105A or 105B) coupled to an asset 104 may scan, during a scanning window, for wireless broadcasts (e.g., wireless broadcasts 122 and/or 123) from beacon devices 102 and 103 located at fixed locations. The wireless broadcast 122 or 123 may include data, such as identifiers, in a data packet. Further, the wireless broadcast 122 or 123 may be an advertisement broadcast using a wireless communication protocol conforming of a low energy wireless personal network (PAN) standard, such as a Bluetooth® Low Energy (BLE) standard. The asset tag (105A or 105B) may have limited memory resources to store all the wireless broadcasts. The wireless broadcasts (e.g., wireless broadcast 122 or 123) received by the asset tag (105A or 105B) may not all be from beacon devices or may be from beacon devices outside a specified distance from the asset tag (105A or 105B) (e.g., proximity). The asset tag (105A or 105B) may filter the wireless broadcasts to generate a subset of the wireless broadcasts. The filtering may be based on at least one of signal strength of the wireless broadcast or an identifier indicating an unapproved device having transmitted the wireless broadcast. The asset tag (105A or 105B) identifies from the wireless broadcasts one or more beacon devices (e.g., two beacon devices, such as beacon devices 102 and 103) that are in the closest distance to the asset tag (105A or 105B) using the signal strength of the wireless broadcasts (e.g., wireless broadcasts 122 and 123). The asset tag (105A or 105B) parses the data packet of the closest beacon device (e.g., beacon device 102) for a beacon identifier and the data packet of the next closest beacon device (e.g., beacon device 103) for another beacon identifier. The asset tag (105A or 105B) creates an updated data packet, using a wireless communication protocol conforming to a low energy wireless PAN standard, and transmits an advertisement broadcast including the updated data packet to a hub 106. The updated data packet may include the beacon identifier of the closest beacon device, the beacon identifier of next closest beacon device, and an asset tag identifier. The hub 106 may transmit data from the updated packet to a server computer system (e.g., server 108), where the data may be used to determine the real-time location of the asset 104.

It should be noted that a wireless communication protocol conforming to the Bluetooth Low Energy® (BLE) (also referred to as Bluetooth Smart®) standard is used for purposes of illustration, rather than limitation. It should be appreciated that other wireless communication protocols may be used, such as protocols conforming to the Bluetooth® wireless standard (also referred to as Classic Bluetooth®), ZigBee® wireless standard, Wi-Fi® wireless standard, ultra-wideband (UWB) wireless standard, or other current or future standards. It should be noted that Bluetooth® shall refer to at least Bluetooth® Low Energy and Classic Bluetooth®, unless otherwise noted. It should also be noted that in one embodiment, the wireless communication protocol may a short range wireless communication protocol compatible with short range wireless communications (e.g., approximately 100 m or less) in a short range wireless network.

The asset tag device 105A may scan for the wireless broadcasts 122 and 123 from respective beacon devices 102 and 103, during as scanning window. The scanning window may be a window of time during which a device, such as asset tag device 105A, scans for a wireless broadcast. The window of time may be any length of time. Scanning may occur once, at intervals, periodically, or continuously as described herein. For example, the scanning window may be 10 seconds and asset tag device 105A may perform a scan 3 times a minute. The wireless broadcasts received by asset tag device 105A may be from devices other than beacon device 102 and 103. For example, asset tag device 105A may receive wireless broadcasts from beacon devices in other areas or from devices using the same wireless communication protocol used by the beacon devices 102 and 103. The asset tag device 105A may filter the scanned wireless broadcast to generate a subset of the wireless broadcasts based on signal strength of the wireless broadcast (e.g., received signal strength indication (RSSI)) and/or an identifier indicating an unapproved device having transmitted the wireless broadcast. Additional details of the filtering will be discussed below with respect to FIGS. 3-4. In one example, generating a subset of the wireless broadcasts may include choosing the N number of devices with the highest wireless broadcast signal strength and disregarding the other received wireless broadcasts.

Asset tag device 105A may identify, within the subset of the wireless broadcast, at least one wireless broadcast in view of an indication that a beacon device having transmitted the wireless broadcast is within a specified distance from asset tag device 105A. Distance may refer to an actual measurable distance (and/or direction) or may refer to a relative distance of one device to the asset tag relative to another device to the asset tag (e.g., one device is closer to the asset tag than the other device). In one example, the actual distance may be specified by for example an administrator. In one embodiment, the indication that of the beacon device is within a specified distance is the signal strength of the wireless broadcast. In one example, the asset tag device 105A determines the received signal strength indicator (RSSI) of each of wireless broadcast of the subset of the wireless broadcasts. The asset tag device 105A sorts the subset of wireless broadcasts by for example, RSSI. RSSI may be a measurement of the power present in the received wireless broadcast. RSSI may serve as an indirect indication of a specified distance of a beacon device, such as beacon device 102 and/or 103, relative to asset tag device 105A. Asset tag device 105A may measure the RSSI of wireless broadcasts. From the sorted wireless broadcasts, asset tag device 105A may identify the beacon devices closest in distance from the asset tag device 105A by choosing the wireless broadcast from a beacon device with the highest RSSI and another wireless broadcast from another beacon device and with the next highest RSSI. In one example, when there is only wireless broadcasts received from one beacon device, asset tag device 105A may choose the one beacon device without sorting the broadcasts. Additional details of the identifying will be discussed below with respect to FIGS. 3, 4, and 6.

Asset tag device 105A may parse the data packet to identify a beacon identifier from the identified wireless broadcasts. The parsing may be at least in part performed during the scanning or filtering. Alternatively, the parsing may be performed after the scanning.

Asset tag device 105A may create a new data packet including a beacon identifier and an asset tag identifier associated with the asset. In one example, the new packet may include the beacon identifier of beacon device 102, the beacon identifier of beacon device 103, and the asset tag identifier of asset tag device 105A. Asset tag device 105A may transmit the new data packet in wireless broadcast 125 to hub 106. Hub 106 may prepare and send the data to server 108 (also referred to as server computer system). In one example, the Hub 106 can prepare the data by aggregating data from multiple asset tag devices. In another example, the Hub 106 can prepare the data by reformatting the data into a format used by the server 108. In another example, the Hub 106 can prepare the data by reformatting data in different asset tag devices to have a common format. Server 108 may use the data to determine information, such as location information, about asset 104. Although the wireless communication protocol used by the beacon devices (i.e., beacon devices 102 and 103) and asset tag device 105A is described as being the same wireless communication protocol, it should be appreciated that the beacon device 102, beacon device 103, and asset tag device 105A may transmit using the same and/or different wireless communication protocol.

Beacon 102 and/or 103 may transmit a wireless broadcast using an advertisement broadcast during windows of time or continuously. A window of time may be a fixed period of time during which a device (e.g., beacon device) performs an action, such as transmitting a wireless broadcast. The broadcast may occur once, at intervals, or periodically. Alternatively, beacon device 102 and/or 103 may transmit a wireless broadcast using a response broadcast. For example, asset tag device 105A can request information (e.g., beacon identifiers) from the surrounding beacon devices. In response, beacon device 102 and/or 102 may communicate the data to the asset tag device 105A using a response broadcast. In one embodiment, the response broadcast is unicast to asset tag device 105A. In another example, the beacon device 102 and/or 103 may transmit an advertisement broadcast to devices located within a threshold radius relative to the beacon device's fixed location. Information, such as beacon identifiers, may be received by devices upon the device entering the associated radius. In another example, beacon devices 102 and/or 103 may serve as a checkpoint used to determine that an asset has passed the beacon device.

Beacon 102 and 103 have been described in connection with beacon device using the iBeacon® technology for purposes of illustration, rather than limitation. In other examples, beacon device 102 or 103 may be an active radio frequency identification device (RFID), a passive RFID, an infrared device, a motion sensor, sonar or sonic device, and/or a near field communication (NFC) device.

As described herein, asset tag device 105A can be coupled to asset 104. The asset tag device 105A may communicate with at least the beacon devices 102 and/or 103, hub 106, sever 108, repeaters (not shown), and/or asset 104. In one example, the asset tag device 105A may be coupled to an individual, such as medical personnel in a hospital environment (also referred to as facility). Asset tag device 105A may be attached to an employee identification badge or attached to or integrated into an electronic device, such as a wristband or watch, worn by the individual. In another example, an asset tag manager 105B may be software integrated into a third party device, such as a mobile phone or tablet. The asset tag manager 105B may leverage at least part of the hardware and/or software resources of the third party device to perform the functions of an asset tag. In should also be appreciated that an asset tag manager 105B may be compatible with any device, software platform, and/or operating system.

Asset tag device 105A may broadcast using an advertisement broadcast during a window of time or continuously. The broadcast may occur once, at intervals, or periodically. An asset tag device 105A may broadcast upon an occurrence of an event, such as the creation of new data packet. Alternatively, asset tag device 105A may broadcast using a response broadcast. For example, hub 106 may request information (e.g., a data packet containing one or more beacon identifiers and/or asset tag identifier) from the surrounding asset tags. In response, asset tag device 105A may communicate the information to the hub 106 using a response broadcast. In one embodiment, the response broadcast is unicast to hub 106. It should be appreciated that asset tag device 105A may broadcast to any device, such as hub 106, a repeater (not shown), or to server 108, within the broadcast radius of asset tag device 105A.

Hub 106 (also referred to as a communication hub) may refer to device that connects multiple electronic devices. Hub 106 may include functionality of a conventional network hub, as well as additional functionality. For example, hub 106 may receive, filter, analyze, modify, and/or transmit data to and from multiple devices using wireless and/or wired communication and/or a combination thereof. Hub 106 may transmit received data to multiple ports, similar to a conventional network hub. Hub 105 may perform functions of a network switch and may receive, process, and forward data only to a destination device that needs to receive it (rather than broadcasting the data to each of its ports). Hub 106 may also function as a wireless access point (AP) and allow wireless devices to connect using a wireless communication protocol (e.g., the Wi-Fi® protocol). Hub 106 may provide a hotspot, a physical location offering internet access, over a wireless local area network (WLAN) through the use of another device such as a router to connect to an internet service provider. Hub 106 may also function as a router to forward data packets between multiple computer networks. Hub 106 may perform software define networking (SDN) functions. For example, hub 106 may function similar to a Dynamic Host Configuration Protocol (DHCP) server that may assign an internet protocol (IP) address to a device (e.g., approved device), attempting to use a network, such as a network using the Wi-Fi® technology associated with hub 106. An internet protocol (IP) table may be configured to route data from devices within a range of IP addresses to one location and/or through a particular channel (or interface) and route data from devices within another range of IP addressed to another location and/or through another channel (or interface).

In one embodiment, hub 106 may have one or more communication channels. A communication channel may refer to a transmission medium (or a path provided by a transmission medium) used to convey an information signal, such as a data packet. Each communication channel may be a transmission medium for different communication protocols (wired and/or wireless communication protocols). Additionally, several communication channels may be the transmission mediums for the same communication protocols. A communication channel may be wired and/or wireless. Hub 106 may include corresponding hardware and/or software for each communication channel. For example, hub 106 may include several wireless communication channels using a wireless communication protocol conforming to a low energy PAN standard, such as a Bluetooth® protocol (i.e., a channel conforming to the Bluetooth® standard able to transmit and receive signals), several wireless communication channels using a wireless communication protocol conforming to a wireless local area network (WLAN) standard, such as the Wi-Fi® protocol, as well as wireless communication channels conforming to other standards, such as a cellular protocol, and an Ethernet protocol. Hub 106 may have an interface for each channel capable of transmitting and/or receiving in the communication protocol associated with the channel. For example, hub 106 may include one or more separate antennas for each channel and/or one or more integrated antennas. Hub 106 may include a PAN antenna, such as a Bluetooth® antenna, and or a WLAN antenna, such as a Wi-Fi® antenna, a wired Ethernet port, and/or a cellular antenna (e.g., multiple-input and multiple-output (MIMO) antenna).

In one embodiment, hub 106 may receive data from multiple source devices, filter and modify the data, and send the modified data through a cellular network and/or wired network (e.g., local area network (LAN)). A cellular network (e.g., mobile network) may be a wireless network distributed over areas (e.g., cells), each served by at least one fixed-location transceiver (e.g., cell site or base station). Each cell may use a different set of frequencies from neighboring cells to avoid interference and provide bandwidth within each cell. The cellular network may use any mobile telecommunications technology such as third generation (3G), fourth generation (4G), and fifth generation (5G) of mobile telecommunications technology. In another example, hub 106 may receive data in data packets conforming to a wireless communication protocol of a low energy wireless PAN standard, such as the BLE® and/or conforming to a wireless communication protocol of a WLAN standard, such as Wi-Fi® and transmit data to the server 108 using cellular communication protocols on a cellular network. In another example, hub 106 may receive data in data packets conforming to the BLE® and/or Wi-Fi® and transmit data to another local server (not shown) using a wired Ethernet cable (e.g., in a LAN).

In one embodiment, hub 106 may be located at a selected location within a facility, such as on each floor of a hospital environment (e.g., facility). Hub 106 may be located at select locations in the hospital environment so as to provide communication coverage throughout the environment. In one example, hub 106 may be located in high traffic areas or along routes or paths that the asset 104 may frequently move along. In another example, the locations can be predefined locations selected during the construction of an environment. In another example, the locations can be selected to provide a desired coverage area, such as a wing of a hospital environment.

In one embodiment, hub 106 may provide a secure private network for devices (such as server 108, asset tag device 105A, or asset 104) to communicate with the hub 106. For example, hub 106 may provide a secure wireless area network (WLAN), secure PAN, or Private Wide Area Network (PWAN) to communicate with a device, such as an asset tag device 105A and/or asset 104. In another example, hub 106 may be a gateway or access point for the asset 104 and/or asset tag device 105A to access information stored on the server 108. For example, hub 106 maybe a network switch enabling asset 104 to access a secure server, such as electronic medical records (EMRs), hospital information system (HIS) information, or an active directory of a hospital server. The devices in the WLAN may use the Wi-Fi® technology and IEEE 802.11 standards defined by the Wi-Fi Alliance. Alternatively, the devices in the WLAN may use other technologies and standards. Similarly, the devices in the PAN or WPAN may use the Bluetooth® technology and IEEE 802.15 standards defined by the Bluetooth Special Interest Group. Alternatively, the devices in the secure PAN may use other technologies and standards. The WAN or PWAN can be used to transmit data over long distances and between different LANs, WLANs, metropolitan area networks (MANs), or other localized computer networking architectures.

In one embodiment, hub 106 may be configured to transmit and receive data using one or more wireless communication protocols. For example, hub 106 may be configured to receive data via a BLE® communication channel and/or a Wi-Fi® communication channel from a device, such as a repeater, and communicate the data to server 108 via a cellular communication channel or to a cloud-based service. Hub 106 may include a multiband antenna and/or multiple antennas to communicate on the different communication channels.

In one embodiment, hub 106 may prepare data for transmission to another device, such as server 108. For example, hub 106 may parse, compressing, secure (e.g., encrypt), and format the data for the consumption by server 108 and/or a cloud-based storage device (not shown).

In another embodiment, hub 106 may include a network compliance device configured to run a Health Level 7 (HL7) engine. HL7 may refer to a set of international standards for transfer of clinical and administrative data between software applications used by various healthcare providers. HL7 may provide a framework for the exchange, integration, sharing and retrieval of data used by healthcare providers. The HL7 engine may format information to an HL7 electronic medical record (EMR) standard. HL7 may provide a framework for the exchange, integration, sharing and retrieval of electronic health information. Hub 106 may use a HL7 formatting engine to aggregate data received, format the data to an HL7 standard, and communicate the formatted data to server 108.

Although not illustrated in FIG. 1B, an asset management system may also include repeaters. A repeater may refer to an electronic device that receives a signal and retransmits the signal, often at a higher power. A repeater may receive a data packet from asset tag device 105A and relay the data to hub 106 or another repeater. A repeater may also act as a bridge to receive data formatted in one wireless communication protocol (e.g., a PAN protocol such as Bluetooth® low energy) and re-transmit in another wireless communication protocol (e.g., a WLAN protocol, such as Wi-Fi®). The repeater may be used by device to tether (e.g., using a PAN or WLAN protocol) to the Internet. The repeaters may be configured as a network of repeaters, such as nodes in a piconet. A piconet may be a wireless personal area network (WPAN) formed by a device (e.g., Bluetooth® device) serving as a master in the piconet and one or more other devices (e.g., other Bluetooth® devices) serving as slaves. For example, a hospital may have multiple repeaters located at different locations in the hospital. The repeaters may receive data from asset tag device 105A, beacon device 102, and/or beacon device 103 and relay the data to hub 106. A repeater may relay the data directly to the hub 106 or indirectly relay the data to hub 106 via one or more other repeaters. In one embodiment, each floor or department of a hospital environment may include a hub, such as hub 106 to receive information from one or more repeaters that provide wireless coverage of the floor. A repeater may be powered by a batter, plugged a wall socket, or powered by any other manner. A repeater may be a small form factor device, such as the size of human child's fist.

Server 108 may be a computing device such as server computer, a desktop computer, or a laptop computer, or a portable computing device such as, but not limited to, mobile telephones, personal digital assistants (PDAs), portable media players, netbooks, tablet computers, portable gaming consoles, portable televisions, electronic book readers, and the like. Although a single server (e.g., server 108) is illustrated in FIG. 1B, any number of servers may be present in an AMS.

Server 108 may be a server computer that is part of an online infrastructure system. Examples of an online infrastructure include a cloud computing platform that may allow multiple users from multiple client systems to access different components or computer resources of the cloud computing platform. The online infrastructure may provide physical and/or virtual resources, such as access to services, servers, or other such resources, to client systems. Examples of services (or functionality) provided by the online infrastructure may include, but are not limited to, access to data stored on storage devices, provisioning of virtual machines, software services, physical servers, etc.

Server 108 may store, process, and or analyze data received from hub 106, as well as beacon device 102 and 103, and asset tag device 105A. In one embodiment, the server may use the beacon identifiers and asset tag identifiers to determine the real-time location of an asset (e.g., real-time location system (RTLS)).

In one embodiment, server 108 may determine the location of asset 104 from the beacon identifier of beacon device 102 and/or beacon device 103, and the asset tag identifier. The server 108 may also record a time stamp indicating when the beacon identifiers were received by asset tag device 105A. Server 108 may store data mapping the location of a beacon device in a facility to a specific beacon identifier. Additionally, sever 108 may store additional data mapping an asset tag identifier to an asset. Accordingly, the beacon identifier and asset tag identifier may be correlated, using the mapping data, to a location in an environment. The location may be the area 110 and/or include a location within area 110 where the asset tag device 105A and associated asset 104 are located (e.g., the middle of area 110).

In one embodiment, the server 108 may include an application programming interface (API), such as a representational state transfer (REST) application program interface (API) interface, to enable applications to retrieve and present data, such as asset data and/or management data, to users. For example, an application may include a user interface with a map of a facility. The application may access the asset data and/or management data and determine the locations of one or more assets in the facility. The application may display the locations of the asset to a user. In another example, the application may query or search the asset data and/or management data to determine user requested data, such as location information of an asset, usage information of an asset, and so forth.

In another embodiment, server 108 may receive battery data indicating battery usage information and/or battery life information for an asset 104, asset tag device 105A, and/or beacon devices 102 and 103. Server 108 may use the battery data to determine a trend in the amount of time a battery of the device may be used, an estimated remaining battery life, battery errors, when to replace a battery, and so forth. For example, asset tag device 105A may receive a battery identifier in a wireless broadcast from beacon device 102 and 103. When creating a data packet, asset tag may include the battery identifier of each beacon device and/or a battery identifier for asset tag device 105A. The battery data, including the battery identifiers may be transmitted to hub 106. A battery identifier may include information such as remaining battery life, battery consumption, and/or battery usage rate of an associated device.

In another embodiment, data such as software updates or patches may be communicated from the server 108 to a hub 106, asset 104, asset tag device 105A, and/or beacon devices 102 and 103.

Figure 1C:
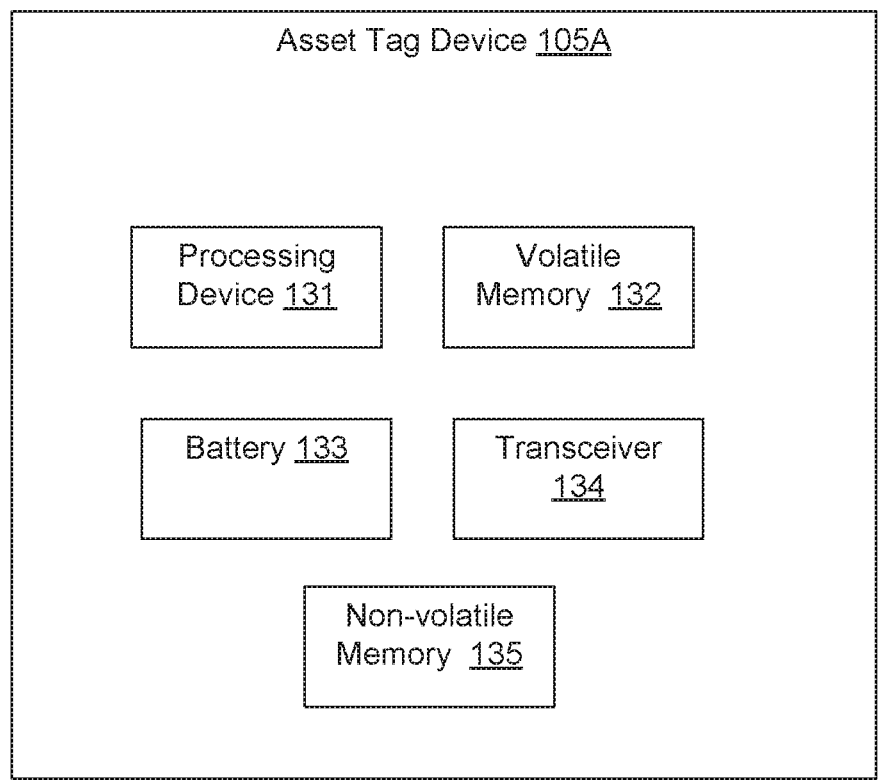
FIG. 1C illustrates an asset tag device, according to one embodiment.

FIG. 1C illustrates an asset tag device, according to one embodiment. Asset tag device 105A may include one or more components such as a processing device 131, volatile memory 132, battery 133, transceiver 134, and/or non-volatile memory 135. Asset tag device 105A may include one or more of the above components. If should be appreciated that the one or more of the components may be integrated as a single component. For example, processing device 131 and transceiver 134 may be integrated on a single integrated circuit. The components may be coupled using a circuit board (not shown). Transceiver 134 may include one or more antennas. Asset tag device 105A may be further described with respect to FIG. 2.

FIG. 2 illustrates an asset tag device, according to one embodiment. Asset tag device 200 is an example of discrete hardware asset tag. Asset tag device 200 may include some or all the features described in regards asset tag device 105A of FIG. 1B and other included figures. It should be noted that asset tag device 200 illustrated as a discrete hardware asset tag is provided for purposed of illustration, rather than limitation. For example, an asset tag may be integrated into another hardware device or implemented using an asset tag manager on a third party device.

Asset tag device 200 may include an external casing, such as casing 202. Casing 202 may be made of numerous materials, such as a hard plastic or other polymer. Asset tag device 200 may be a small form factor device, the size of a quarter or less, and weighing less than an ounce. The asset tag device 200 may include an input/output (I/O) terminal 204 to send and receive data. Additionally, I/O terminal 204 may be used to recharge a rechargeable battery internal to asset tag device 200. The I/O terminal 204 may conform to the micro universal serial bus (USB), USB, or other type of standard. The battery of asset tag device 200 may also be recharged by wireless charging. Asset tag device 200 may include electronic hardware such as a radio (e.g., Bluetooth® radio), a processing device (e.g., Microcontroller (MCU)), an antenna, and a battery. The asset tag device 200 may also include memory either as part of the processing device and/or a discrete component.

Figure 3:
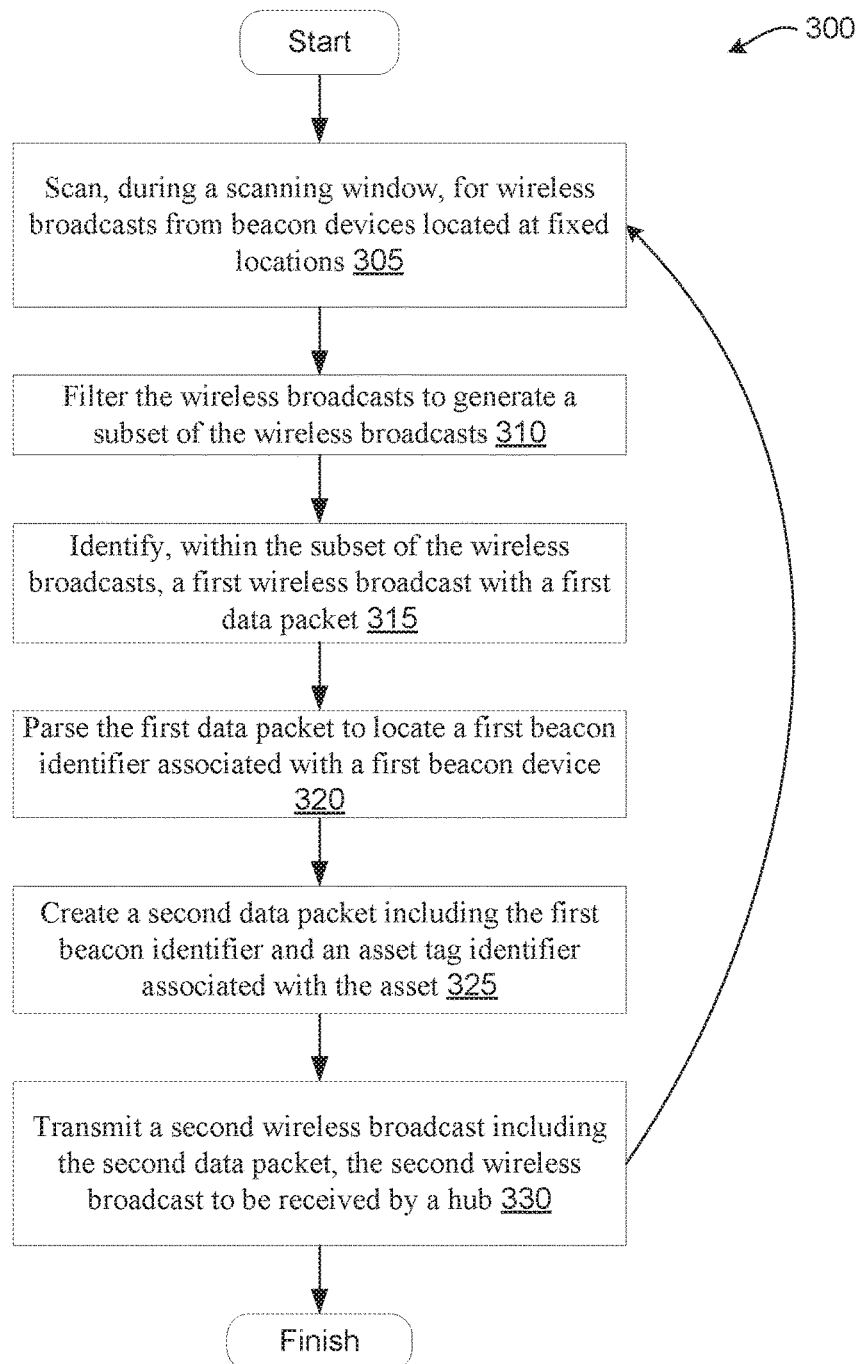
FIG. 3 illustrates a method of scanning for wireless broadcasts by an asset tag, according to one embodiment.

FIG. 3 illustrates a method of scanning for and transmitting wireless broadcasts by an asset tag, according to one embodiment. The method 300 may be performed by processing logic that comprises hardware (e.g., circuitry, dedicated logic, programmable logic, microcode, etc.), software (such as instructions run on a processing device), or a combination thereof. The method 300 may be performed all or in part by asset tag manager 105B.

Method 300 begins at block 305 where processing logic executing the method scans, during a scanning window, for wireless broadcasts from beacon devices located at fixed locations. In one example, the wireless broadcasts are advertisement broadcasts from beacon devices at different fixed locations. In another example, the wireless broadcasts are response broadcasts. In another example, the wireless broadcasts use a wireless communication protocol conforming to a low energy wireless personal area network standard. The wireless broadcast includes identifiers in a data packet. The scanning may performed processing logic of an asset tag coupled to an asset. Additional details of scanning are discussed above at least with respect to FIGS. 1A and 1B.

Method 300 continues to block 310, where processing logic filters the wireless broadcasts to generate a subset of the wireless broadcasts. The filtering may be based on signal strength of the wireless broadcast and/or an identifier indicating an unapproved device having transmitted the wireless broadcast. The subset of the wireless broadcasts may be stored in a memory. In one example the subset of the wireless broadcasts may be limited to a fixed number of the wireless broadcasts, for example 10 wireless broadcast. Limiting the number of the subset of the wireless broadcast may be at least in part influenced by the limited memory resources and/or computational resources (e.g., processing device) of the asset tag. Additionally, the number may be influenced by a sample size of wireless broadcasts that permit accurate location determination by the server. In one example, the filtering is performed at least in part during the scanning. In another example, the filtering may occur at least in part after the scanning. It should be noted that the wireless broadcasts may be cleared from memory prior to the next cycle of scanning performed by the asset tag. Additional details of filtering are discussed above at least with respect to FIG. 1A, 1B and below with respect to FIG. 5.

Method 300 continues to block 315, where processing logic identifies, within the subset of the wireless broadcasts, a wireless broadcast (e.g., first) with a data packet. The wireless broadcast may be identified in view of an indication that the first beacon device is within a specified distance from to the asset tag, the first beacon device having transmitted the wireless broadcast. The indication may be the signal strength of the wireless broadcast. The signal strength may indicate a relative distance (e.g., relative to other wireless broadcasts from other devices) of the beacon device from an asset tag. Additional details of identifying are discussed above at least with respect to FIG. 1A, 1B and below with respect to FIGS. 4 and 6.

Method 300 continues to block 320, where processing logic parses the data packet (e.g., first) to locate a beacon identifier (e.g., first) associated with a beacon device (e.g., first). In one example the beacon identifier includes the major identifier and/or minor identifier. It should be appreciated that the beacon identifier may be one or more different identifiers in data packet. The parsing may occur at least in part during the filtering. It should be appreciated that filtering may include parsing, for example to find identifiers indicating an unapproved device. Additionally, the parsing may be in part performed during the scanning or after the scanning. Additional details of filtering are discussed above at least with respect to FIG. 1A, 1B and below with respect to FIG. 4.

Method 300 continues to block 325, where processing logic creates a data packet (also referred to as second, updated or new data packet) including the beacon identifier (e.g., first) and an asset tag identifier associated with the asset. The asset tag identifier may be locally stored at the asset tag. It should also be appreciated that the data packet may be created to include additional data, such as additional identifiers, other beacon identifiers, battery identifiers, etc. In one example, processing logic creates a data packet configured to be an advertisement broadcast. In another example, processing logic may create a data packet configured for a response broadcast. Additional details of filtering are discussed above at least with respect to FIG. 1A, 1B and below with respect to FIGS. 4 and 7.

Method 300 continues to block 330, where processing logic transmits a wireless broadcast comprising the data packet (e.g., second). The wireless broadcast may be received by a hub, a repeater, server, and/or other device. In one example, the wireless broadcast may be an advertisement broadcast. In another example, the wireless broadcast may be a response broadcast. The wireless broadcast may be for a window of time. The wireless broadcast may be in a wireless communication protocol conforming to a wireless communication protocol of a low energy wireless personal area network (PAN) standard. After transmitting the broadcast for a window of time, processing logic may return to scanning as described at block 305. Additional details of transmitting are discussed above at least with respect to FIGS. 1A and 1B.

Figure 4:
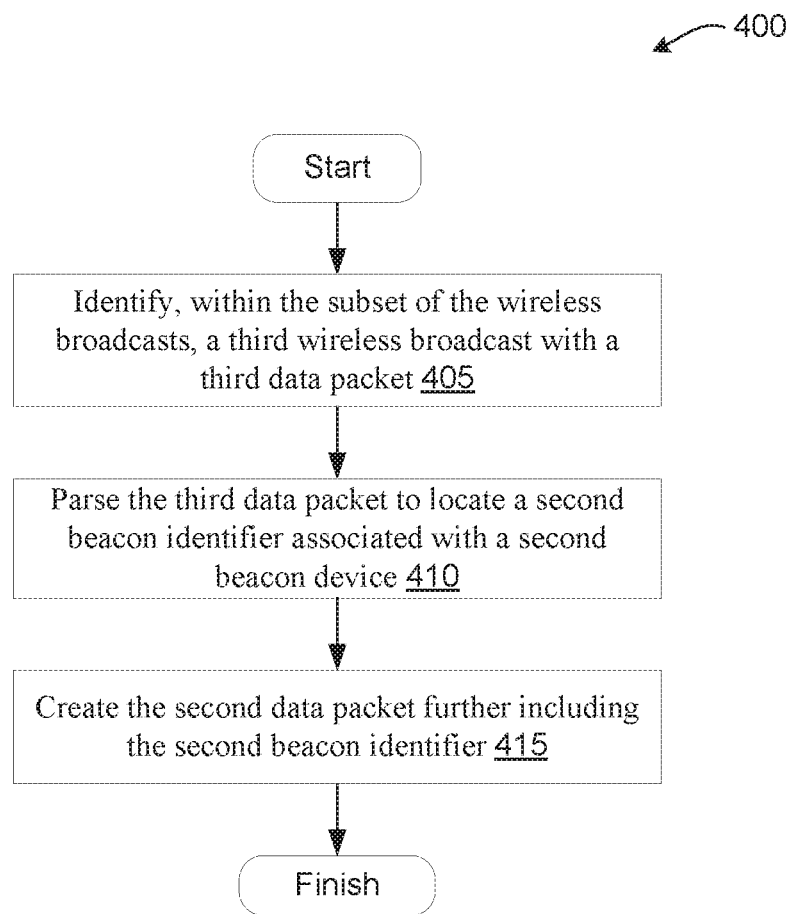
FIG. 4 illustrates a method of scanning for wireless broadcasts by an asset tag, according to another embodiment.

FIG. 4 illustrates a method of scanning for and transmitting wireless broadcasts by an asset tag, according to another embodiment. The method 400 may be performed by processing logic that comprises hardware (e.g., circuitry, dedicated logic, programmable logic, microcode, etc.), software (such as instructions run on a processing device), or a combination thereof. The method 400 may be performed all or in part by asset tag manager 105B.

Method 400 begins at block 405 where processing logic executing the method identifies, within the subset of the wireless broadcasts, another wireless broadcast (e.g., third) with another data packet (e.g., third). The wireless broadcast may be identified in view of an indication that another beacon device (e.g., second beacon device) is within a specified distance to the asset tag, the beacon device having transmitted the wireless broadcast. The indication that another beacon device is within a specified distance may be the signal strength of the wireless broadcast. It should be noted that the identifying of block 405 may performed as part of the identifying of block 315 of method 300, above. In one embodiment, two or more beacon devices, each at a fixed location, may define an area. Additional details of filtering are discussed above at least with respect to FIGS. 1A, 1B, 3 and below with respect to FIG. 6.

Method 400 continues to block 410, where processing logic parses the data packet to locate another beacon identifier (e.g., second) associated with another beacon device (e.g., second beacon device). Similar to method 300, in one example, the beacon identifier may include the major identifier and/or minor identifier. It should be appreciated that the beacon identifier may be one or more different identifiers in data packet. The parsing may be part of the parsing described in block 320 of method 300, above. The parsing may occur at least in part during the filtering. It should be appreciated that filtering may include parsing, for example to find identifiers indicating an unapproved device. Additionally, the parsing may be in part performed during the scanning or after the scanning.

Method 400 continues to block 415, where processing logic creates the data packet (e.g., second) to further include the beacon identifier of the other beacon device. In another embodiment, processing logic may create a separate data packet with the beacon identifier of the other beacon device and the asset tag identifier. It should also be appreciated that the data packet may be created to include additional data, such as additional identifier, other beacon identifier, battery identifiers, etc. In one example, processing logic creates a data packet configured to be an advertisement broadcast. In another example, processing logic may create a data packet configured for a response broadcast.

Figure 5:
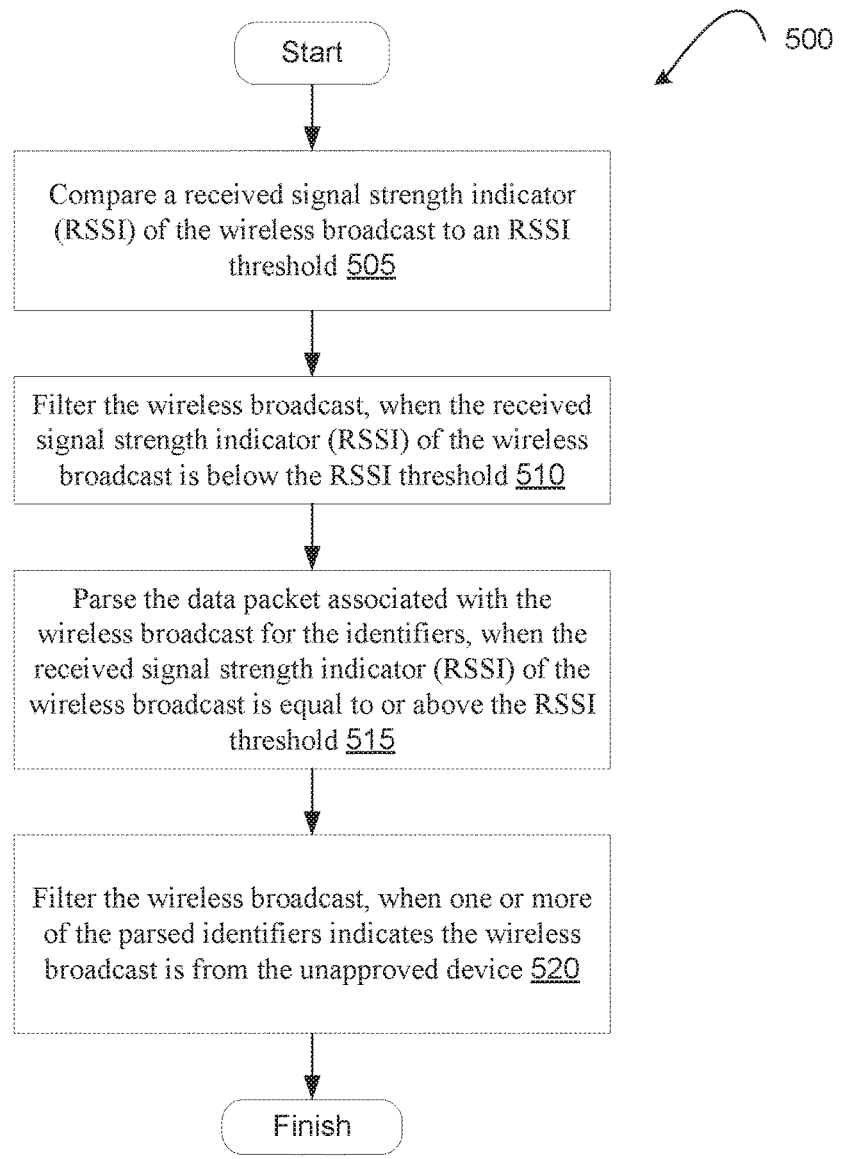
FIG. 5 illustrates a method of filtering wireless broadcasts by an asset tag, according to one embodiment.

FIG. 5 illustrates a method of filtering wireless broadcasts by an asset tag, according to one embodiment. The method 500 may be performed by processing logic that comprises hardware (e.g., circuitry, dedicated logic, programmable logic, microcode, etc.), software (such as instructions run on a processing device), or a combination thereof. The method 500 may be performed all or in part by asset tag manager 105B.

Method 500 begins at block 505, where processing logic executing the method compares a received signal strength indicator (RSSI) of the wireless broadcast to an RSSI threshold. Method 500 continues to block 510, where processing logic filters the wireless broadcast, when the received signal strength indicator (RSSI) of the wireless broadcast is below the RSSI threshold. The RSSI threshold may be set by a developer. For example, the RSSI threshold may be set to −110 dBm, or any other value. Received wireless broadcasts with RSSI below the RSSI threshold may be from beacon devices from outside an area of interest, and may not include data useful to determine location of the asset tag. Determining the RSSI may be additionally discussed in reference to FIG. 6.

Method 500 continues to block 515, where processing logic parses the data packet associated with the wireless broadcast for the identifiers, when the received signal strength indicator (RSSI) of the wireless broadcast is equal to or above the RSSI threshold. It should be noted that the parsing may be performed as part of the parsing discussed above with respect to method 300 and/or method 400. It also should be noted that the parsing may performed with or without processing logic performing block 505 and 510, described above.

Method 500 continues to block 520, where processing logic filters the wireless broadcast, when one or more of the parsed identifiers indicate the wireless broadcast is (e.g., originated) from the unapproved device. It should be appreciated that processing logic may receive wireless broadcasts from multiple sources. Processing logic may not only receive broadcasts from the beacon devices located in an area. Processing logic may receive broadcasts from other beacon device as well as devices transmitting data using the same wireless communication protocol that processing logic is scanning for. An unapproved device may include a device that is not a beacon device. As noted above, wireless broadcasts may include multiple identifiers, such as company identifiers, source device information identifiers, identifiers of other manufacturing specific data (e.g., manufacturer identifier), wireless broadcast identifier (e.g., advertisement indicator identifier), beacon identifier (e.g., a major identifier (ID), minor identifier), battery identifier, etc. Processing logic may parse one or more identifiers and compare them to an approved list of identifiers. For example, processing logic may parse the data packet to look for a company identifier and a manufacturing identifier. When at least one of the company identifier and manufacturing identifier do not match approved identifiers, processing logic may determine the wireless broadcast is from an unapproved device, and may be filtered. It should be appreciated than any identifier or combination of identifiers may be used as an indication that a wireless broadcast is from an unapproved device.

Figure 6:
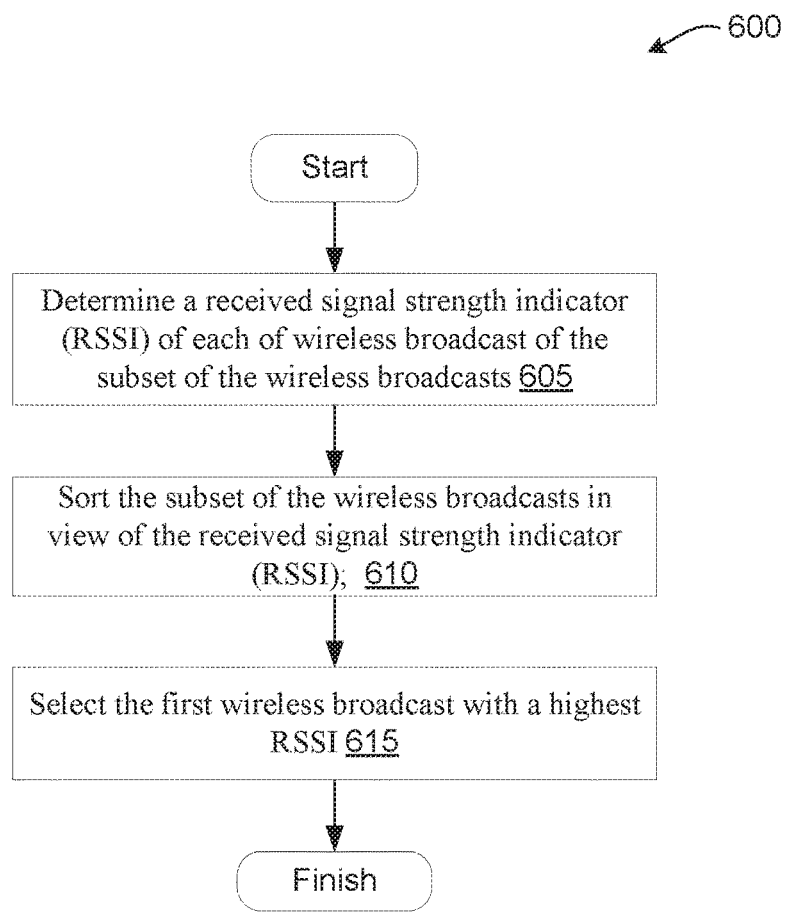
FIG. 6 illustrates a method of identifying a wireless broadcast, according to one embodiment.

FIG. 6 illustrates a method of identifying a wireless broadcast, according to one embodiment. The method 600 may be performed by processing logic that comprises hardware (e.g., circuitry, dedicated logic, programmable logic, microcode, etc.), software (such as instructions run on a processing device), or a combination thereof. The method 600 may be performed all or in part by asset tag manager 105B.

Processing logic may use signal strength as an indication that a beacon device having transmitting a wireless broadcast is within a specified distance from an asset tag. In the one embodiment, the signal strength may be the RSSI a wireless broadcast.

Method 600 begins at block 605, where processing logic executing the method determines the received signal strength indicator (RSSI) of each wireless broadcast of the subset of the wireless broadcast. It should be appreciated that the determination of wireless broadcasts of the subset of wireless broadcast may be performed, at least in part, during filtering as discussed with respect to method 300 and 400. In one embodiment, the RSSI is determined (e.g., measured) by the device (e.g., asset tag) receiving the wireless broadcast. The device may include an indicator of RSSI (e.g., the RSSI identifier indicating an RSSI value of the wireless broadcast) in the data packet associated with the wireless broadcast. The RSSI identifier may include a value of the received signal strength.

Method 600 continues to block 610, where processing logic may sort the subset of the wireless broadcasts in view of a received signal strength indicator (RSSI). For example, the wireless may be sorted 1 through 10 starting with the wireless broadcast having the strongest RSSI and ending with the wireless broadcast with the weakest RSSI. Method 600 continues to block 615, where processing logic may select the wireless broadcast as the broadcast with the highest RSSI from the sorted wireless broadcasts. It should be noted that in some embodiments, processing logic may determine the RSSI of the wireless broadcast of the subset of wireless broadcast, and determine the wireless broadcast with the highest RSSI without sorting. Additional details of filtering are discussed above at least with respect to FIGS. 1A, 1B, 3, and 4.

In another embodiment, processing logic may use signal strength to identify the two or more beacon devices closest distance from the asset tag. Processing logic may determine the RSSI of wireless broadcasts for two or more beacon devices. Processing logic may sort the subset of the wireless broadcasts in view of a received signal strength indicator (RSSI). For example, the wireless may be sorted 1 through 10 starting with the wireless broadcast having the strongest RSSI and ending with the wireless broadcast with the weakest RSSI. As described above with respect to block 615, processing logic may select the wireless broadcast with the highest RSSI, which would be from the first beacon device. To find the second beacon device defining the area, processing logic may select the wireless broadcast with the highest RSSI from a beacon device different from the first beacon device. The same process may to find the wireless broadcasts when more than two beacon devices. Processing logic may identify and differentiate beacon devices using the beacon identifier, such as major identifier and minor identifier, contained in the received data packets.

Figure 7:
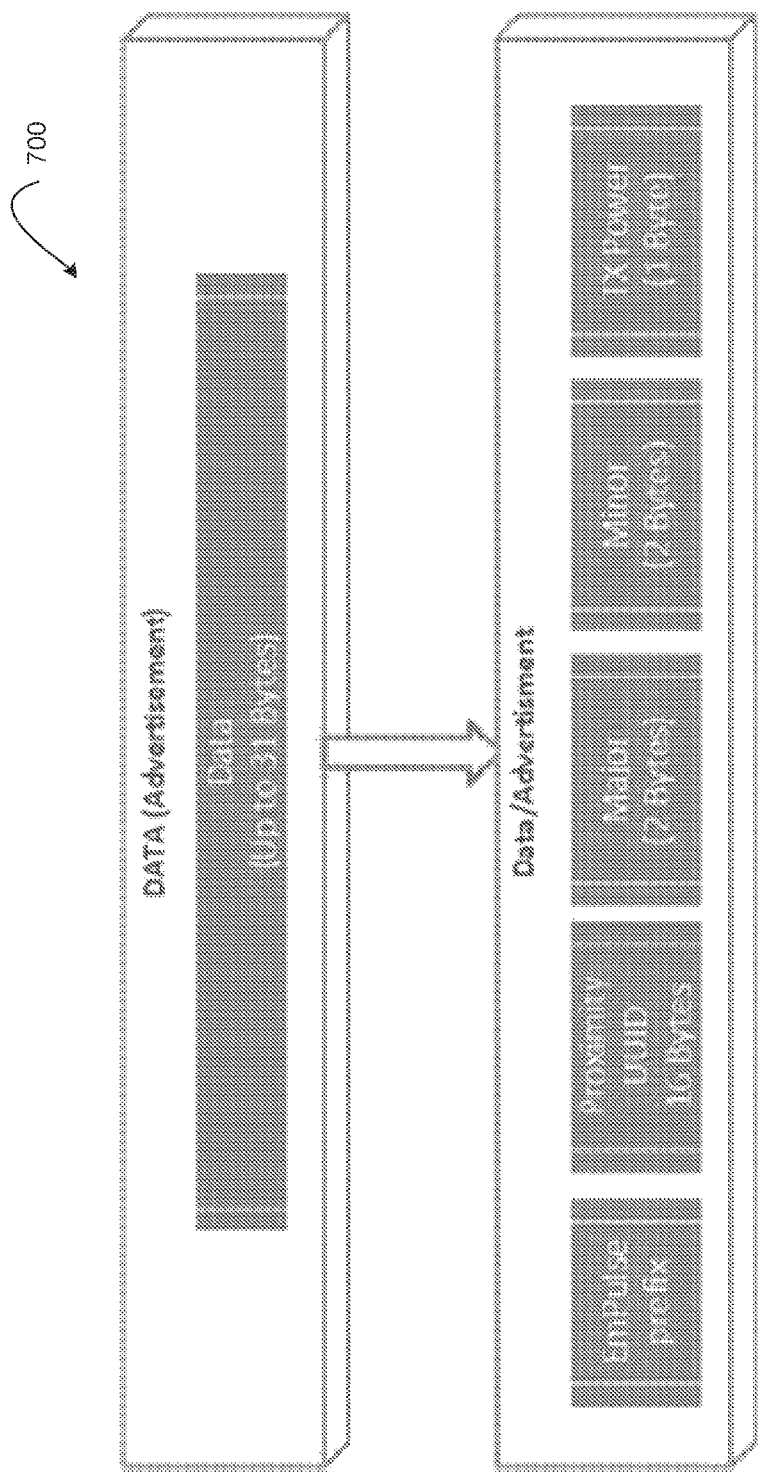
FIG. 7 illustrates a format of a data packet, according to one embodiment.

FIG. 7 illustrates a format of a data packet, according to one embodiment. Data packet 700 may be an example of an advertisement broadcast from a beacon device, such as beacon device 102 and/or 103 of FIG. 1, in a wireless communication protocol compliant with a wireless communication protocol of a low energy wireless personal area network (PAN) standard. It should be appreciated that data packet 700 may be from another device, such as an asset tag, and include additional or different data than illustrated in FIG. 7.

In one embodiment, data packet 700 may include a fixed beacon prefix (e.g., EmPulse prefix). Data packet 700 may include a proximity UUID identifier. In one example, an asset tag may scan for beacon devices with a UUID assigned to beacon devices fixed to a known location. In another example, an asset tag may filter out beacon devices based on manufacturing specific information (e.g., identifiers) and/or device names.

In one embodiment, a data packet from a beacon device may include a major identifier (e.g., number) and/or a minor identifier (e.g., number). In one example, the major identifier is used to group a related set of beacon devices. The major identifier may be 2 bytes, such as 0x0049 or 73. In another example, beacon devices for an area, floor, entity, etc. may use the same major identifier. The minor identifier may be used to identify individual beacon devices. A minor identifier may be 2 bytes, such as 0x000A or 10. In one example, each beacon device in an AMS system may have different minor identifiers. An asset tag may include the received major identifier and minor identifier in a data packet to a hub/server. The sever may use the data to determine a location of an asset. In example, the major identifier and/or minor identifier may be serialized numbers independent from the relationship between beacon devices or locations of beacon devices. Another device, such as a sever, may keep a record of the serial number of a beacon device and the corresponding location of the beacon device, and use the record to determine location of an asset.

In another embodiment, a data packet may include a signal strength identifier, such as a transmit (TX) power identifier. In one example, the TX power identifier may indicate a transmit power of the beacon device transmitting a wireless broadcast. For example, the transmit power identifier may be 0xC5=197, where 2's complement=256−197=−59 dBm. An asset tag may determine a distance (e.g., proximity) between the beacon device and the asset tag by comparing received signal power (e.g., RSSI) with the transmit power identifier. The asset tag may determine a distance between the beacon device and the asset tag as the distance causing the transmit power to decrease to the received signal power. In another embodiment, the signal strength identifier may be an RSSI.

Figure 8:
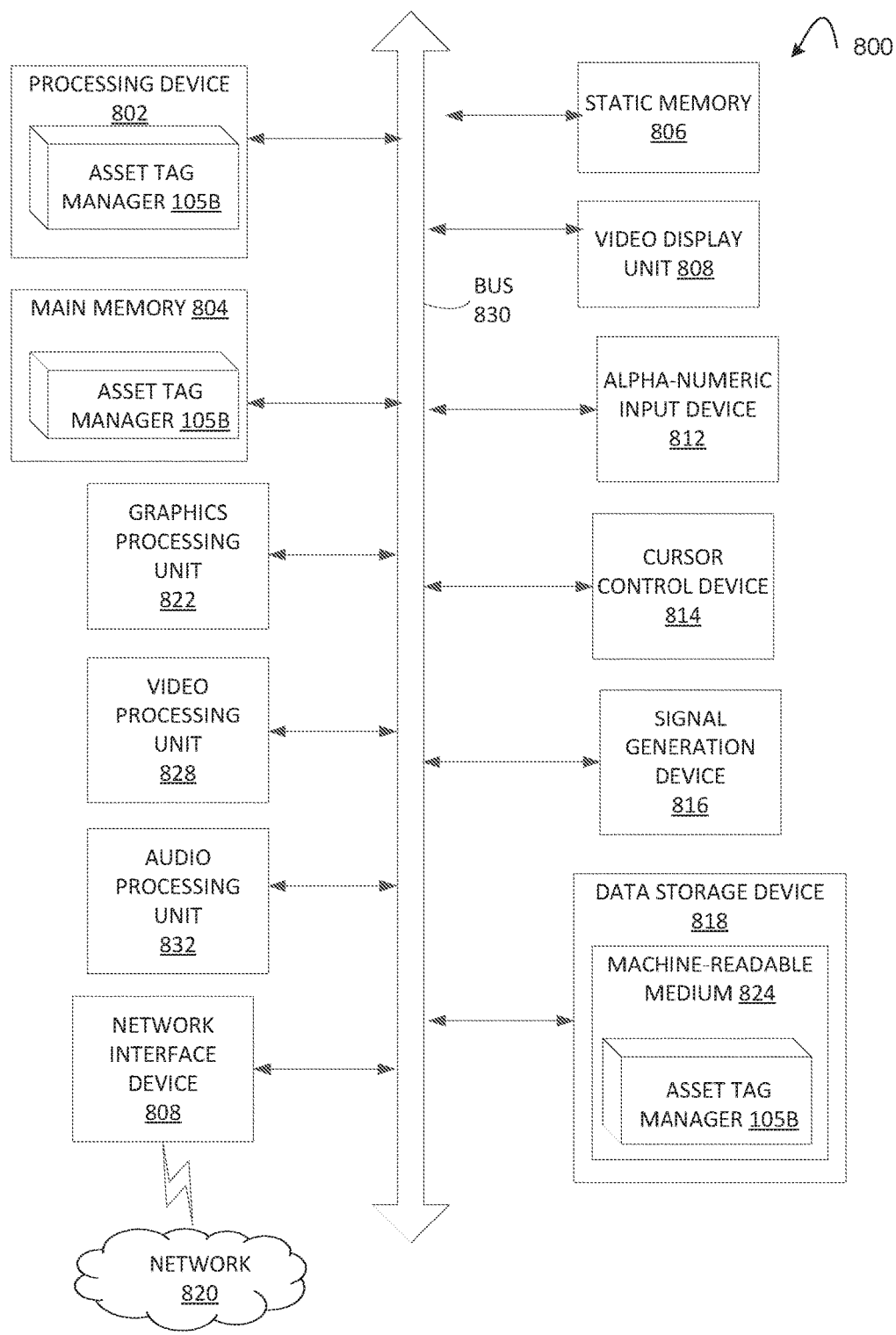
FIG. 8 illustrates a block diagram of a machine, according to one embodiment.

FIG. 8 illustrates a diagrammatic representation of a machine in the exemplary form of a computer system 800 within which a set of instructions for causing the machine to perform any one or more of the methodologies discussed herein, may be executed. In alternative implementations, the machine may be connected (e.g., networked) to other machines in a LAN, an intranet, an extranet, or the Internet. The machine may operate in the capacity of a server or a client machine in a client-server network environment, or as a peer machine in a peer-to-peer (or distributed) network environment. The computer system 800 may also be the asset tag device, or a host device hosting an asset tag manager 105B, as described herein. The machine may be a personal computer (PC), a tablet PC, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" can also be taken to include any collection of machines that individually or jointly execute a set (or multiple sets) of instructions to perform any one or more of the methodologies discussed herein.

The exemplary computer system 800 includes a processing device (processor) 802, a main memory 804 (e.g., read-only memory (ROM), flash memory, dynamic random access memory (DRAM) such as synchronous DRAM (SDRAM) or Rambus DRAM (RDRAM), etc.), a static memory 806 (e.g., flash memory, static random access memory (SRAM), etc.), and a data storage device 818, which communicate with each other via a bus 830.

Processing device 802 represents one or more general-purpose processing devices such as a microprocessor, central processing unit, microcontroller, or the like. More particularly, the processing device 802 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processing device 802 may also be one or more special-purpose processing devices such as an application specific integrated circuit (ASIC), a field programmable gate array (FPGA), a digital signal processor (DSP), network processor, or the like. The processing device 802 is configured to execute instructions 826 for performing the operations and steps discussed herein.

The computer system 800 may further include a network interface device 822. The computer system 800 also may include a video display unit 808 (e.g., a liquid crystal display (LCD), a cathode ray tube (CRT), or a touch screen), an alphanumeric input device 810 (e.g., a keyboard), a cursor control device 814 (e.g., a mouse), and a signal generation device 816 (e.g., a speaker).

The data storage device 818 may include a machine-readable storage medium 824 on which is stored one or more sets of instructions (e.g., software including asset tag manager 105B) embodying any one or more of the methodologies or functions described herein. The instructions may also reside, completely or at least partially, within the main memory 804 and/or within the processing device 802 during execution thereof by the computer system 800, the main memory 804 and the processing device 802 also constituting computer-readable storage media. The instructions may further be transmitted or received over a network 820 via the network interface device 834.

While the machine-readable storage medium 824 is shown in an exemplary implementation to be a single medium, the term "computer-readable storage medium" should be taken to include a single medium or multiple media (e.g., a centralized or distributed database, and/or associated caches and servers) that store the one or more sets of instructions. The term "computer-readable storage medium" can also be taken to include any medium that is capable of storing, encoding or carrying a set of instructions for execution by the machine and that cause the machine to perform any one or more of the methodologies of the present disclosure. The term "computer-readable storage medium" can accordingly be taken to include, but not be limited to, solid-state memories, optical media, and magnetic media.

In the foregoing description, numerous details are set forth. It can be apparent, however, to one of ordinary skill in the art having the benefit of this disclosure, that the present disclosure may be practiced without these specific details. In some instances, well-known structures and devices are shown in block diagram form, rather than in detail, in order to avoid obscuring the present disclosure.

Some portions of the detailed description have been presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those that may use physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "scanning", "filtering", "identifying", "parsing", "creating," "transmitting," "comparing," "sorting," "selecting," or the like, refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices.

Although the operations of the methods herein are shown and described in a particular order, the order of the operations of each method may be altered so that certain operations may be performed in an inverse order or so that certain operation may be performed, at least in part, concurrently with other operations. In another embodiment, instructions or sub-operations of distinct operations may be in an intermittent and/or alternating manner. The terms "first," "second," "third," "fourth," etc. as used herein are meant as labels to distinguish among different elements and may not necessarily have an ordinal meaning according to their numerical designation.

The disclosure also relates to an apparatus for performing the operations herein. This apparatus may be specially constructed for the required purposes, or it may include a general-purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions.

The words "example" or "exemplary" are used herein to mean serving as an example, instance, or illustration. Any aspect or design described herein as "example' or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Moreover, use of the term "an embodiment" or "one embodiment" or "an implementation" or "one implementation" throughout is not intended to mean the same embodiment or implementation unless described as such.

Reference throughout this specification to "one embodiment" or "an embodiment" means that a particular feature, structure, or characteristic described in connection with the embodiment is included in at least one embodiment. Thus, the appearances of the phrase "in one embodiment" or "in an embodiment" in various places throughout this specification are not necessarily all referring to the same embodiment. In addition, the term "or" is intended to mean an inclusive "or" rather than an exclusive "or."

It is to be understood that the above description is intended to be illustrative, and not restrictive. Many other implementations can be apparent to those of skill in the art upon reading and understanding the above description. The scope of the disclosure should, therefore, be determined with reference to the appended claims, along with the full scope of equivalents to which such claims are entitled.

What is claimed is:

1. A method comprising:
   scanning, by an asset tag manager executing by a processing device during a scanning window, for wireless broadcasts from beacon devices located at fixed locations, wherein:
      a wireless broadcast comprises a beacon identifier in a data packet, and
      the asset tag manager is associated with an asset;
   filtering the wireless broadcasts, by the asset tag manager, to generate a subset of the wireless broadcasts, wherein the filtering is based on at least one of signal strength of the respective wireless broadcast or an identifier indicating an unapproved device having transmitted the wireless broadcast;
   identifying, by the asset tag manager, within the subset of the wireless broadcasts, a first wireless broadcast with a first data packet in view of an indication that a first beacon device is within a specified distance from the asset tag manager, the first beacon device having transmitted the first wireless broadcast;
   parsing, by the asset tag manager, the first data packet to locate a first beacon identifier associated with the first beacon device;
   creating, by the asset tag manager, a second data packet with the first beacon identifier and an asset tag identifier associated with the asset; and
   transmitting a second wireless broadcast comprising the second data packet, the second wireless broadcast to be received by a hub.

2. The method of claim 1, further comprising:
   identifying, by the asset tag manager, within the subset of the wireless broadcasts, a third wireless broadcast with a third data packet in view of the indication that a second beacon device is within a specified distance from the asset tag, the second beacon device having transmitted the third wireless broadcast;
   parsing, by the asset tag manager, the third data packet to locate a second beacon identifier associated with a the second beacon device; and
   creating, by the asset tag manager, the second data packet further comprising the second beacon identifier.

3. The method of claim 1, further comprising storing the subset of the wireless broadcasts in memory, wherein the subset of the wireless broadcasts are limited to a fixed number of the wireless broadcasts.

4. The method of claim 1, wherein the wireless broadcasts are advertisement broadcasts from the beacon devices at different fixed locations.

5. The method of claim 1, wherein parsing the first data packet to locate the first beacon identifier is at least in part performed as part of the filtering the wireless broadcasts or is at least in part performed during the scanning.

6. The method of claim 1, wherein filtering the wireless broadcasts comprises:
   comparing a received signal strength indicator (RSSI) of the wireless broadcast to an RSSI threshold; and
   filtering the wireless broadcast, when the received signal strength indicator (RSSI) of the wireless broadcast is below the RSSI threshold.

7. The method of claim 6, wherein filtering the wireless broadcasts further comprises:
   parsing the data packet associated with the wireless broadcast for the identifiers, when the received signal strength indicator (RSSI) of the wireless broadcast is equal to or above the RSSI threshold; and
   filtering the wireless broadcast, when one or more of the parsed identifiers indicates the wireless broadcast is from the unapproved device.

8. The method of claim 1, wherein the indication of that the first beacon device is within the specified distance from the asset tag is the signal strength of the first wireless broadcast.

9. The method of claim 1, wherein the identifying further comprises:
   determining a received signal strength indicator (RSSI) of a wireless broadcast of the subset of the wireless broadcasts;
   sorting the subset of the wireless broadcasts in view of the received signal strength indicator (RSSI); and
   selecting the first wireless broadcast with a highest RSSI.

10. The method of claim 1, wherein in the wireless broadcasts from the beacon devices and the second wireless broadcast from the asset tag are transmitted using a wireless communication protocol of a low energy wireless personal area network (PAN) standard.

11. The method of claim 1, wherein the asset tag manager executes on the processing device within an asset tag device.

12. An asset tag device comprising:
   an antenna for receiving and transmitting wireless broadcasts;
   a processing device operatively coupled to the antenna; and a memory, coupled to the processing device and storing instructions of an asset tag manager, that the instructions when executed cause the processing device to:
scan, during a scanning window, for wireless broadcasts from beacon devices located at fixed locations, wherein a wireless broadcast comprises a beacon identifier in a data packet, and wherein the to the asset tag manager is associated with an asset;
filter the wireless broadcasts to generate a subset of the wireless broadcasts, wherein the filtering is based on at least one of signal strength of the respective wireless broadcast or an identifier indicating an unapproved device having transmitted the wireless broadcast;
identify, within the subset of the wireless broadcasts, a first wireless broadcast with a first data packet in view of an indication that a first beacon device is within a specified distance from the asset tag manager, the first beacon device having transmitted the first wireless broadcast;
parse the first data packet to locate a first beacon identifier associated with a first beacon device;
create a second data packet with the first beacon identifier and an asset tag identifier associated with the asset; and
transmit a second wireless broadcast comprising the second data packet, the second wireless broadcast to be received by a hub.

13. The asset tag device of claim 12, the processing device further to:
identify, within the subset of the wireless broadcasts, a third wireless broadcast with a third data packet in view of the indication that a second beacon device is within a specified distance from the asset tag, the second beacon device having transmitted the third wireless broadcast;
parse the third data packet to locate a second beacon identifier associated with the second beacon device; and
create the second data packet further comprising the second beacon identifier.

14. The asset tag device of claim 12, wherein to filter the wireless broadcasts, the processing device further to:
compare a received signal strength indicator (RSSI) of the wireless broadcast to an RSSI threshold;
filter the wireless broadcast, when the received signal strength indicator (RSSI) of the wireless broadcast is below the RSSI threshold;
parse the data packet associated with the wireless broadcast for the identifiers, when the received signal strength indicator (RSSI) of the wireless broadcast is equal to or above the RSSI threshold; and
filter the wireless broadcast, when one or more of the parsed identifiers indicates the wireless broadcast is from the unapproved device.

15. The asset tag device of claim 12, wherein to identify, the processing device further to:
determine a received signal strength indicator (RSSI) of a wireless broadcast of the subset of the wireless broadcasts;
sort the subset of the wireless broadcasts in view of the received signal strength indicator (RSSI); and
select the first wireless broadcast with a highest RSSI.

16. A non-transitory machine-readable storage including instruction that, when executed by a processing device, cause the processing device to:
scan, during a scanning window, for wireless broadcasts from beacon devices located at fixed locations, wherein a wireless broadcast comprises a beacon identifier in a data packet, and wherein an asset tag manager is associated with an asset;
filter the wireless broadcasts to generate a subset of the wireless broadcasts, wherein the filtering is based on at least one of signal strength of the respective wireless broadcast or an identifier indicating an unapproved device having transmitted the wireless broadcast;
identify, within the subset of the wireless broadcasts, a first wireless broadcast with a first data packet in view of an indication that a first beacon device is within a specified distance from the asset tag manager, the first beacon device having transmitted the first wireless broadcast;
parse the first data packet to locate a first beacon identifier associated with a first beacon device;
create a second data packet with the first beacon identifier and an asset tag identifier associated with the asset; and
transmit a second wireless broadcast comprising the second data packet, the second wireless broadcast to be received by a hub.

17. The non-transitory machine-readable storage of claim 16, the processing device further to:
identify, within the subset of the wireless broadcasts, a third wireless broadcast with a third data packet in view of the indication that a second beacon device is within a specified distance from the asset tag, the second beacon device having transmitted the third wireless broadcast;
parse the third data packet to locate a second beacon identifier associated with the second beacon device; and
create the second data packet further comprising the second beacon device identifier.

18. The non-transitory machine-readable storage of claim 16, wherein to filter the wireless broadcasts, the processing device further to:
compare a received signal strength indicator (RSSI) of the wireless broadcast to an RSSI threshold; and
filter the wireless broadcast, when the received signal strength indicator (RSSI) of the wireless broadcast is below the RSSI threshold.

19. The non-transitory machine-readable storage of claim 18, wherein to filter the wireless broadcasts, the processing device further to:
parse the data packet associated with the wireless broadcast for the identifiers, when the received signal strength indicator (RSSI) of the wireless broadcast is equal to or above the RSSI threshold; and
filter the wireless broadcast, when one or more of the parsed identifiers indicates the wireless broadcast is from the unapproved device.

20. The non-transitory machine-readable storage of claim 16, wherein to identify, the processing device further to:
determine a received signal strength indicator (RSSI) of a wireless broadcast of the subset of the wireless broadcasts;
sort the subset of the wireless broadcasts in view of the received signal strength indicator (RSSI); and
select the first wireless broadcast with a highest RSSI.

* * * * *